United States Patent [19]
Dervan et al.

[11] Patent Number: 5,874,555
[45] Date of Patent: Feb. 23, 1999

[54] TRIPLE HELICES AND PROCESSES FOR MAKING SAME

[75] Inventors: Peter B. Dervan, San Marino, Calif.; Heinz E. Moser, Reinach, Switzerland

[73] Assignee: California Institute of Technology, Pasadena, Calif.

[21] Appl. No.: 156,957

[22] Filed: Nov. 22, 1993

Related U.S. Application Data

[63] Continuation of Ser. No. 850,503, Mar. 13, 1992, abandoned, which is a continuation-in-part of Ser. No. 115,922, Oct. 30, 1987, abandoned.

[51] Int. Cl.$^6$ .................................................. C07H 21/04
[52] U.S. Cl. .............................. 536/23.1; 435/6; 436/501; 536/24.1; 536/24.3; 536/24.31; 536/24.32; 536/24.33; 536/25.3; 935/77; 935/78
[58] Field of Search .................................... 435/5, 6, 810; 436/501; 536/22.1, 23.1, 24.1, 24.31–24.33, 25.3; 935/77, 78, 88

[56] References Cited

U.S. PATENT DOCUMENTS

| | | | |
|---|---|---|---|
| 4,358,535 | 11/1982 | Falkon et al. | 435/5 |
| 4,563,417 | 1/1986 | Albarella et al. | 435/6 |
| 4,599,303 | 7/1986 | Yabusaki et al. | 435/6 |
| 4,665,184 | 5/1987 | Dervan et al. | 546/109 |
| 4,711,955 | 12/1987 | Ward et al. | 536/29 |
| 4,795,700 | 1/1989 | Dervan et al. | 435/5 |
| 4,828,979 | 5/1989 | Klevan et al. | 435/6 |
| 4,835,263 | 5/1989 | Nguyen et al. | 536/27 |
| 4,837,312 | 6/1989 | Dervan et al. | 536/27 |
| 5,422,251 | 6/1995 | Fresco | 435/91.1 |

FOREIGN PATENT DOCUMENTS

| | | |
|---|---|---|
| 117777 | 9/1984 | European Pat. Off. . |
| 169787 | 1/1986 | European Pat. Off. . |
| 214908 | 3/1987 | European Pat. Off. . |
| 0375408 | 6/1990 | United Kingdom . |
| 8804301 | 6/1988 | WIPO . |

OTHER PUBLICATIONS

Jiricny et al. (1986) Nucleic Acids Res., vol. 14, No. 16 pp. 6579–6590.
Eritja et al. (1986) Nucleic Acids Res., vol. 14, No. 20, pp. 8135–8153.
Le Doan et al. (1987) Nucleic Acids Res., vol. 15, No. 19, pp. 7749–7760.
Marck et al. (1978) Nucleic Acids Res., vol. 5, No. 3, pp. 1017–1028.
Strobel, S.A., et al., "Site–Specific Cleavage of Human Chromosome 4 Mediated by Triple–Helix Formation", *Science* 254:1639–1642, 1991 (Dec. 13).
Strobel, S.A., et al., "Single–side enzymatic cleavage of yeast genomic DNA mediated by triple helix formation", *Nature* 350:172–174, 1991 (Mar. 14).
Beal, P.A., et al., "Second Structural Motif for Recognition of DNA by Oligonucleotide–Directed Triple–Helix Formation", *Science* 251:1360–1363. 1991(Mar. 15).
Horne, D.A., et al., "Effects of an abasic site on triple helix formation characterized by affinity cleaving", *Nucleic Acids Research* 19:4863–4965, 1991 (later than Aug. 9).
Griffin, L.C., et al., "Recognition of Thymine–Adenine Base Pairs by Guanine in a Pyrimidine Triple Helix Motif", *Science* 245:967–971, 1989.

(List continued on next page.)

*Primary Examiner*—Ardin H. Marschel
*Attorney, Agent, or Firm*—Flehr Hohbach Test Albritton & Herbert LLP

[57] ABSTRACT

Oligonucleotides and processes for their use for specific recognition of a target sequence in double-stranded nucleic acid through the formation of a triple helix. The oligonucleotides can bind in a parallel or antiparallel orientation to one of the strands of the target sequence depending upon the sequence composition of the target sequence and oligonucleotide used. The oligonucleotides are used as diagnostic or therapeutic agents through incorporation of an appropriate moiety in one or more nucleotides in the triple helix forming oligonucleotide.

35 Claims, 14 Drawing Sheets

OTHER PUBLICATIONS

Strobel, S.A., et al., "Double–Strand Cleavage of Genomic DNA at a Single Site by Triple–Helix Formation", *J. Am. Chem. Soc.* 110:7927–7929, 1988.

Luebke, K.H., et al., "Nonenzymatic Ligation of Oligodeoxyribonucleotides on a Duplex DNA Template by Triple–Helix Formation", *J. Am. Chem. Soc.* 111:8733–8735, 1989.

Strobel, S.A., et al., "Cooperative Site Specific Binding of Oligonucleotides to Duplex DNA", *J. Am. Chem. Soc.* 111:7286–7287, 1989.

Povsic, T.J., et al., "Triple Helix Formation by Oligonucleotides on DNA Extended to the Physiological pH Range", *J. Am. Chem. Soc.* 111:3059–3061, 1989.

Strobel, S.A., et al., "Site–Specific Cleavage of a Yeast Chromosome by Oligonucleotide–Directed Triple–Helix Formation", *Science* 249:73–75, 1990.

Horne, D.A., et al., "Recognition of Mixed–Sequence Duplex DNA by Alternate–Strand Triple–Helix Formation", *J. Am. Chem. Soc.* 1990, 112:2435–2437, 1990.

Maher, L.J., III., et al., "Inhibition of DNA Binding Proteins by Oligonucleotide–Directed Triple Helix Formation", *Science* 725–730, 1989.

Taylor, J.S., et al., "DNA Affinity Cleaving—Sequence Specific Cleavage of DNA by Distamycin–EDTA·Fe (II) and EDTA–Distamycin·Fe (II)", *Tetrahedron* 40:457–465, 1984.

Moser, H.E., et al., "Sequence–Specific Cleavage of Double Helical DNA by Triple Helix Formation", *Science* 238:645–650, 1987.

Schultz, P.C., et al., "Sequence–specific double–strand cleavage of DNA by penta–N–methylpyrrolecarboxamide–EDTA.Fe (II)", *PNAS* 80:6834–6837, 1983.

Dreyer, G.B., et al., "Sequence–specific cleavage of single–stranded DNA:Oligodeoxynucleotide–EDTA·Fe (II)", *PNAS 82:968–972*, 1985.

Van Dyke, M.M., et al., "Echinomycin Binding Sites on DNA", *Science* 225:1122–1127, 1984.

Hertzberg, R.P., et al., "Cleavage of DNA with Methidiumpropyl–EDTA–Iron (II): Reaction Conditions and Product Analyses", *Biochemistry* 23:3934–3945, 1984.

Hertzberg, R.P., et al., "Cleavage of Double Helical DNA by (Medthidiumpropyl–EDTA) iron (II)", *J. Am. Chem. Soc.* 104:313–315, 1982.

Praseuth, D, et al., "Sequence–specific binding and photocrosslinking of α and β oligodeoxynucleotides to the major groove of DNA via triple–helix formation", *PNAS* 85:1349–1353, 1988.

Francois, J–C., et al., "Sequence–targeted Cleavage of Single– and Double–stranded DNA by Oligothymidylates Covalently Linked to 1,10–Phenanthroline", *J. Biol. Chem.* 264:5991–5898, 1989.

Francois, J–C., et al., "Inhibition of Restriction Endonuclease Cleavage via Triple Helix Formation by Homopyrimidine Oligonucleotides", *Biochemistry* 28:9617–9619, 1989.

Sun, J–S., et al., "Sequence–specific intercalating agents: Intercalation at specific sequences on duplex DNA via major groove recognition by oligonucleotide–intercalator conjugates", *PNAS* 86:9198–9202, 1989.

Zerial, A., et al., "Selective inhibition of the cytophathic effect of type A influenza viruses by oligodeoxynucleotides covalently linked to an intercalating agent", *Nucleic Acids Research* 15:9909–9919, 1987.

Cazenave, C., et al., "Rate of degradation of [α]– and [β]–oligodeoxynucleotides in Xenopus oocytes. Implications for anti–messenger strategies", *Nucleic Acids Research* 15:10507–10521, 1987.

Durland, R.H., et al., "Binding of Triple Helix Forming Oligonucleotides to Sites in Gene Promoters", *Biochemistry* 30:9246–9255, 1991.

Cooney, M., et al., "Site–Specific Oligonucleotide Binding Represses Transcription of the Human c–myc Gene in Vitro", *Science* 241:456–459, 1988.

Williams, N.G., et al., "Dimers, Trimers, and Tetramers of Cytosine with Guanine", *J. Am. Chem.Soc.* 111:7205–7209, 1989.

Letai, A.G., et al., "Specificity in Formation of Triple–Stranded Nucleic Acid Helical Complexes: Studies with Agarose–Linked Polyribonucleotide Affinity Columns", *Biochemistry* 27:9108–9112, 1988.

Broitman, S.L., et al., "Formation of the triple–stranded polynucleotide helix, poly(A·A·U)", *PNAS* 84:5120–5124, 1987.

Lipsett, M.N., "Complex Formation between Polycytidylic Acid and Guanine Oligonucleotides", *J. Biol. Chem.* 2239:1256–1260, 1984.

Llyamchev, V.I., et al., "A stable complex between homopyrimidine oligomers and the homologous regions of duplex DNA", *Nucleic Acids Research* 16:2165–2176, 1988.

Rajagopal, P., et al., "Triple–strand formation in the homopurine:homopyrimidine DNA oligonucleotides $d(G-A)_4$ and $d(T-C)_4$", *Nature* 339:637–640, 1989.

Kohwi, Y., et al., "Magnesium ion–dependent triple–helix structure formed by homopurine–homopyrimidine sequences in supercoiled plasmid DNA", *PNAS* 85:3781–3785, 1988.

Hanvey, J.C., et al., "Site–specific inhibition of EcoRi restriction/modification enzymes by a DNA triple helix", *Nucleic Acids Research* 18:157–161, 1989.

Torrence, P.F., et al., "Triple–Helical Polynucleotides. Mixed Triplexes of the Poly(uridylic acid)·Poly (adenylic acid) ·Poly(uridylic acid) Class", *Biochemistry* 15:724–734, 1976.

Perlgut, L.E., et al., "Formation of triple–stranded bovine DNA in vitro", *Nature* 254:86–87, 1975.

Chu, B.C.F., et al., "Nonenzymatic sequence–specific cleavage of single–stranded DNA", *PNAS* 82:963–967, 1985.

Moffat, A.S., "Triplex DNA Finally Comes of Age", *Science* 252:1374–1375, 1991 (Jun.).

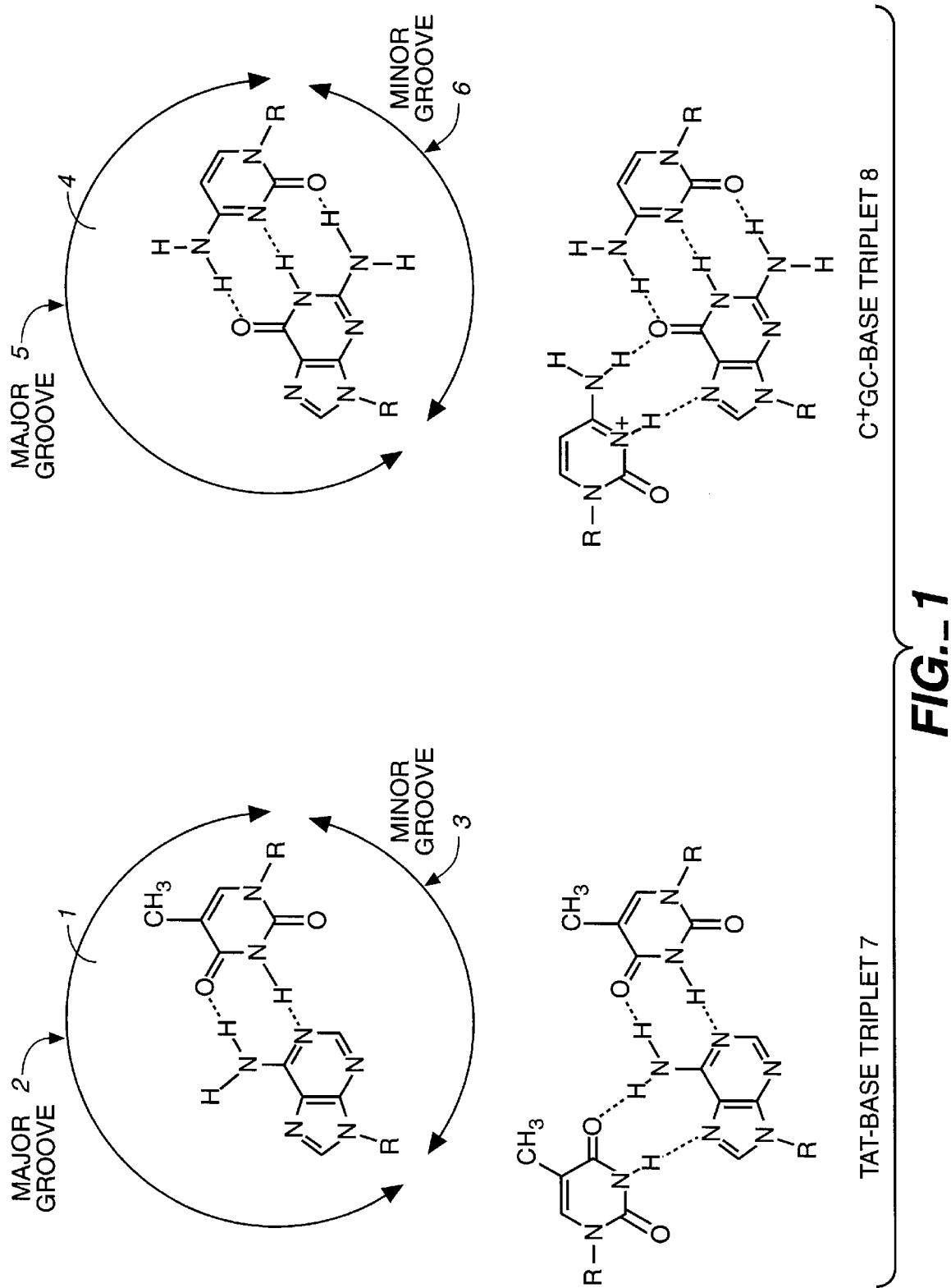
FIG._1

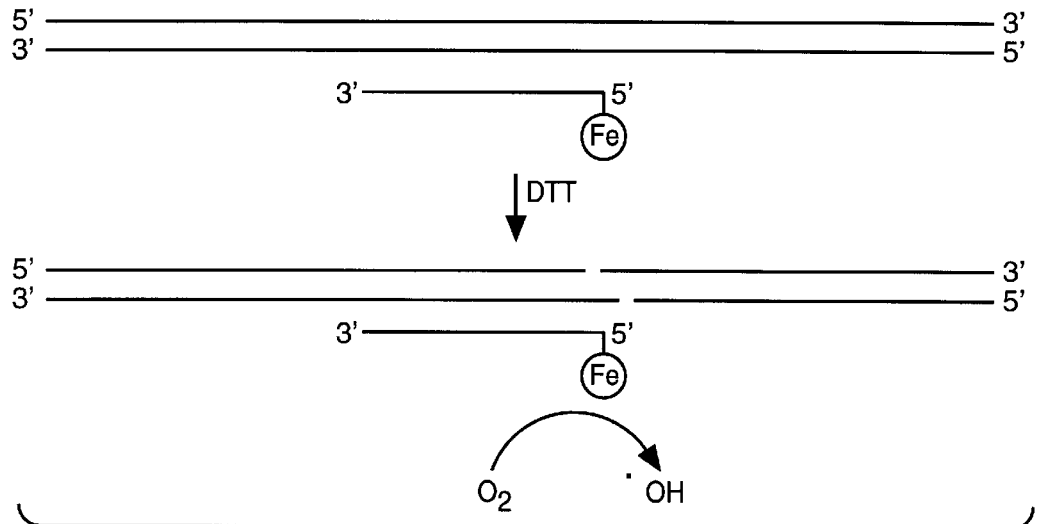
FIG._2
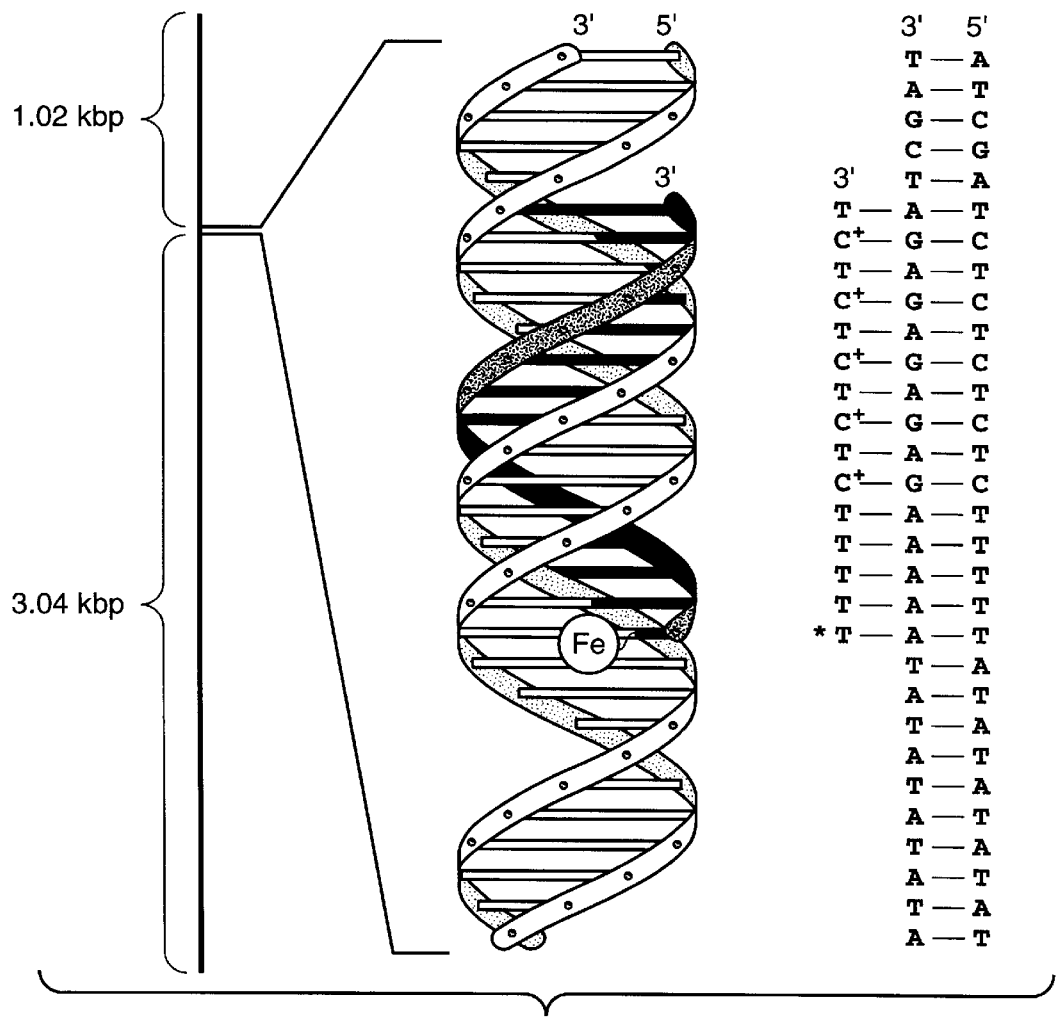
FIG._7

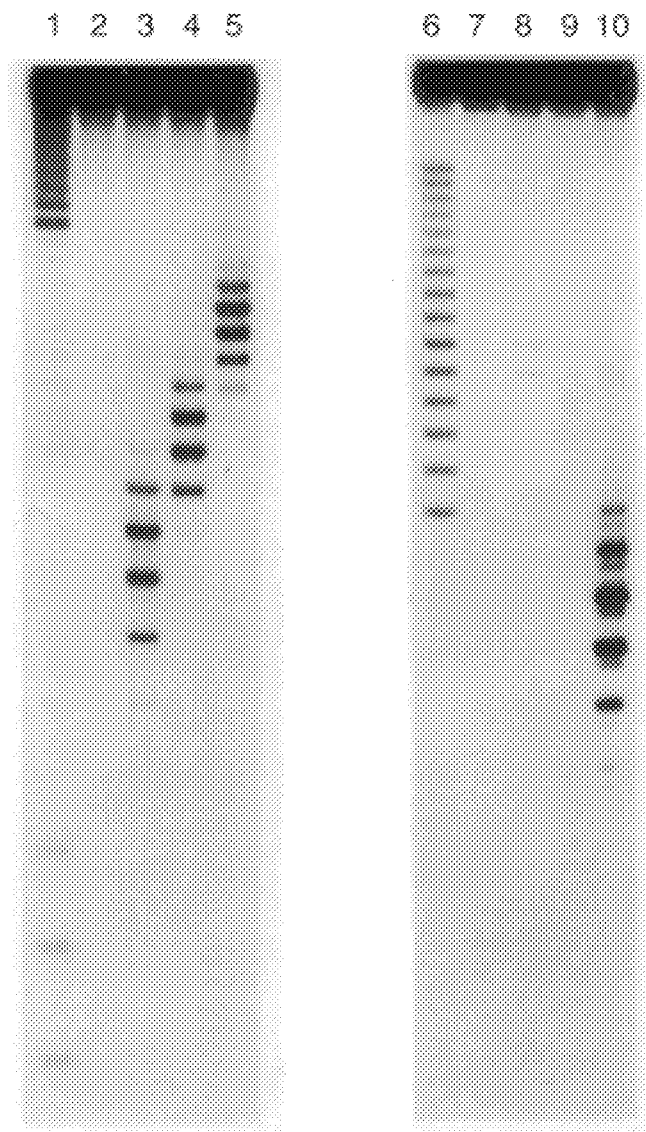
FIG._3A

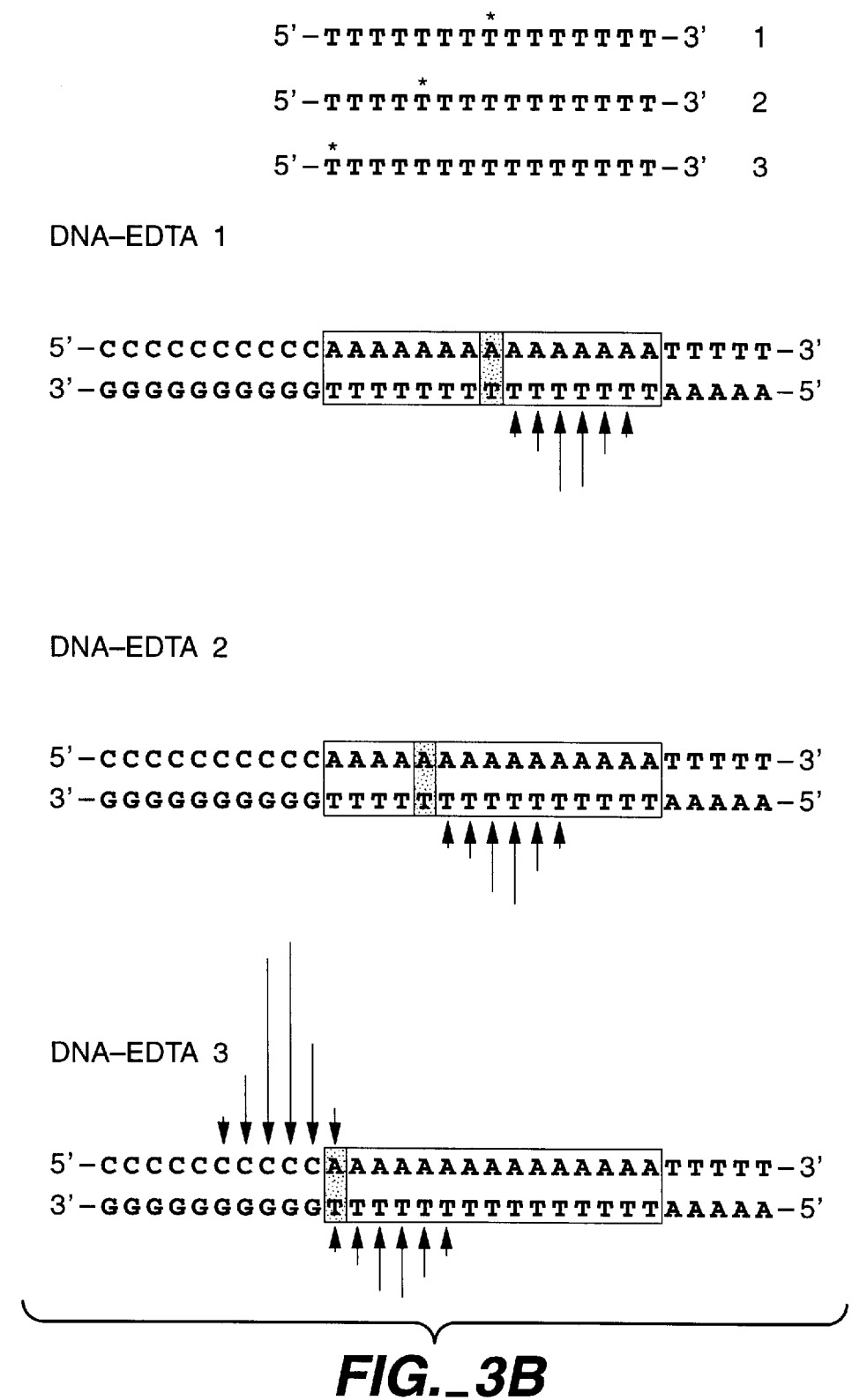
FIG._3B

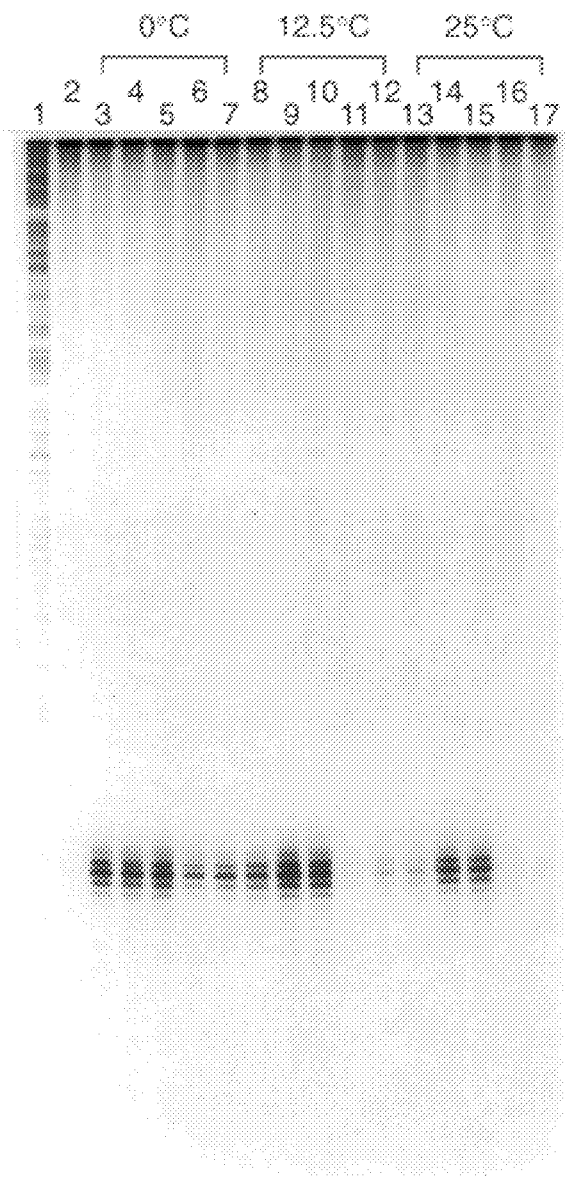
FIG._4A
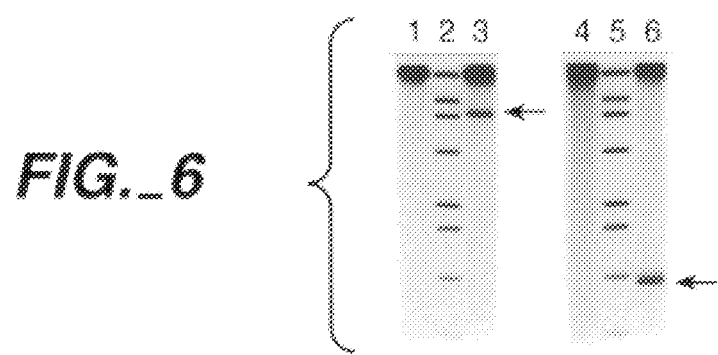
FIG._6

```
5'-TTTTT*CTCTCTCTCT-3'      4
5'-TTTTT*CTCTCTCT-3'        5
5'-TTTTT*CTCTCT-3'          6
5'-TTTTT*CTCTTTCTCT-3'      7
5'-TTTTT*CTCTCCTCT-3'       8
5'-*TTTTTCTCTCTCTCT-3'      9
```
DNA–EDTA 4
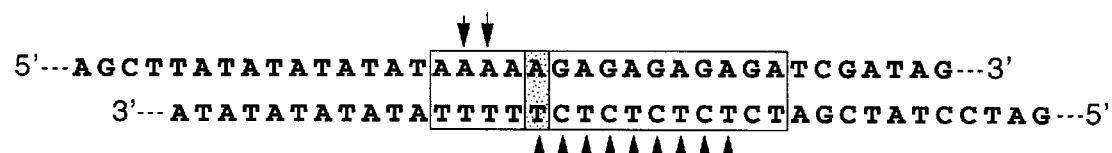
DNA–EDTA 9
628 bp
FIG._4B

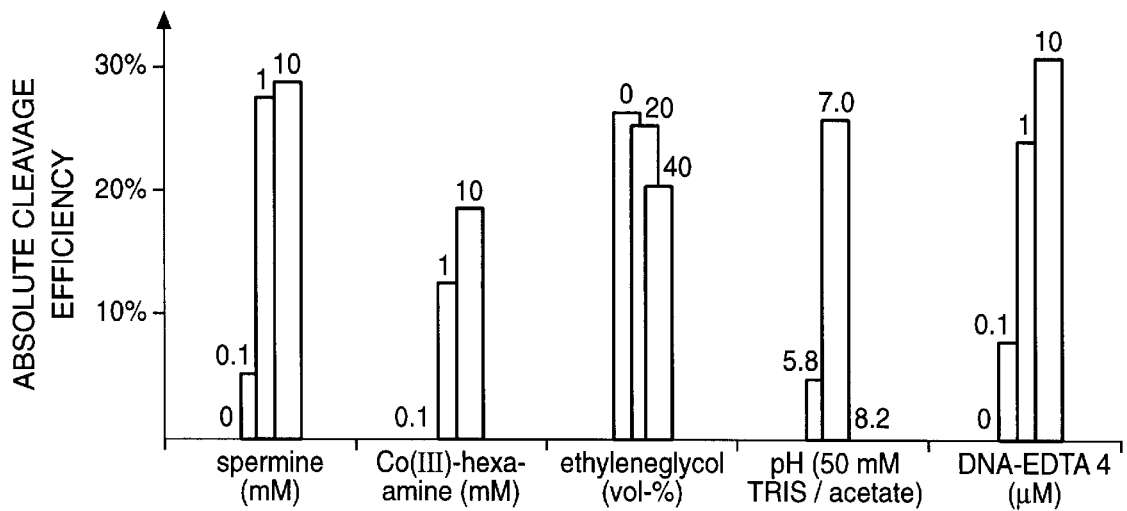
FIG._5A
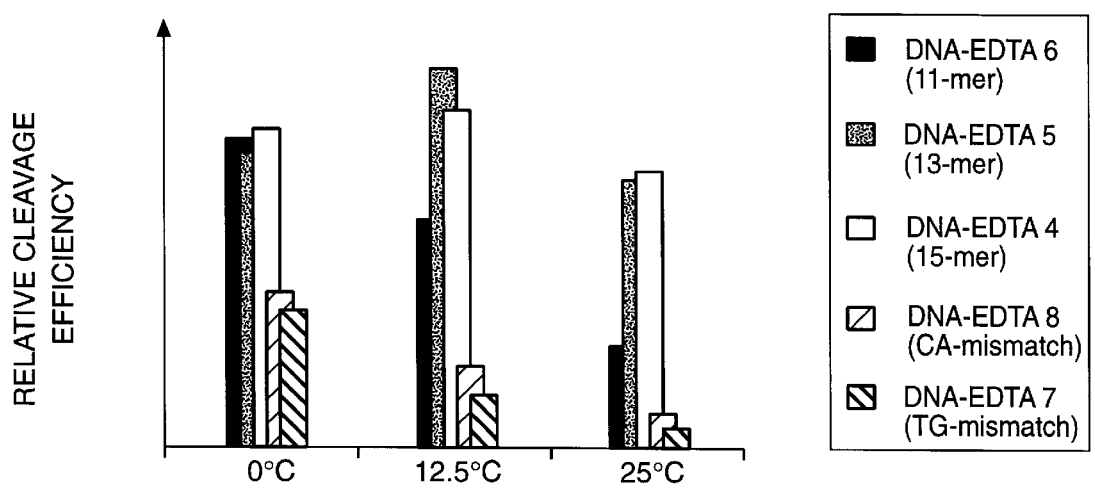
FIG._5B

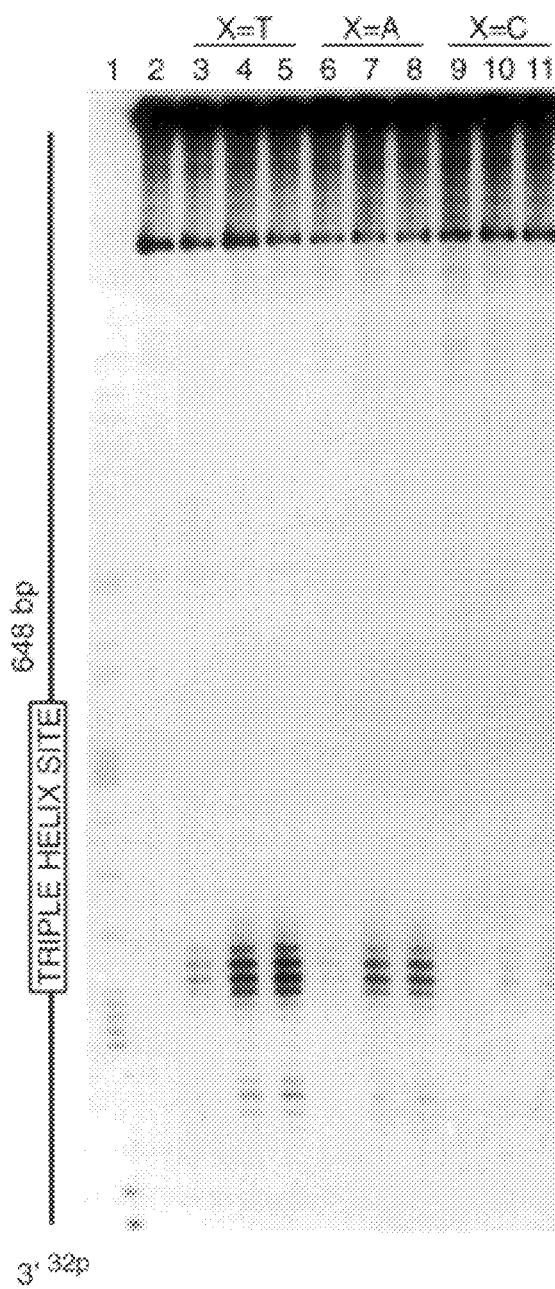
*FIG._8A*
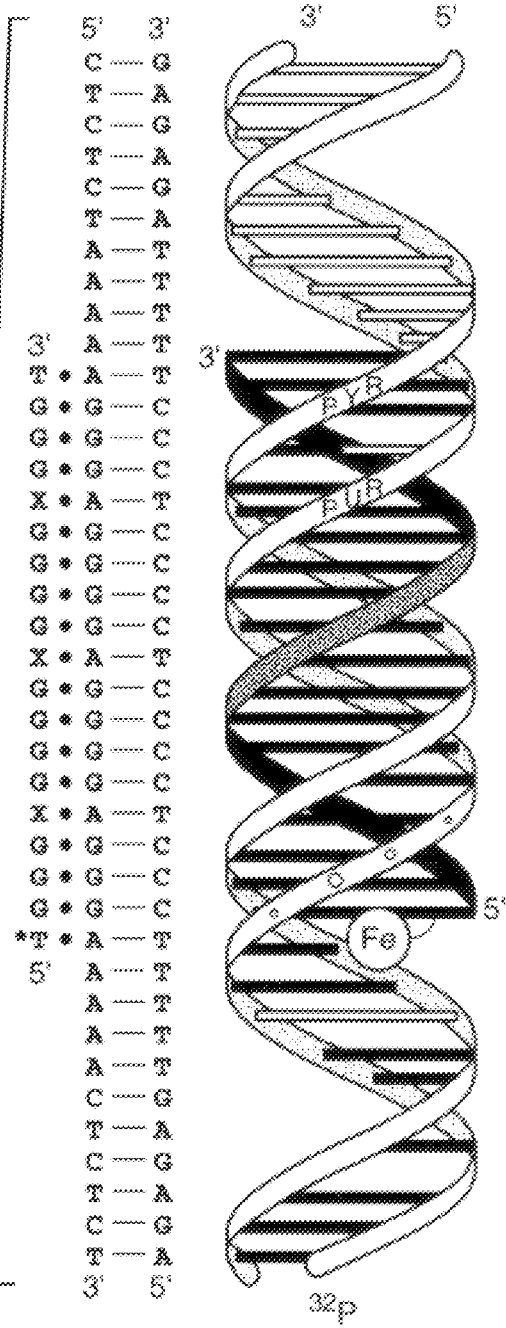
*FIG._8B*

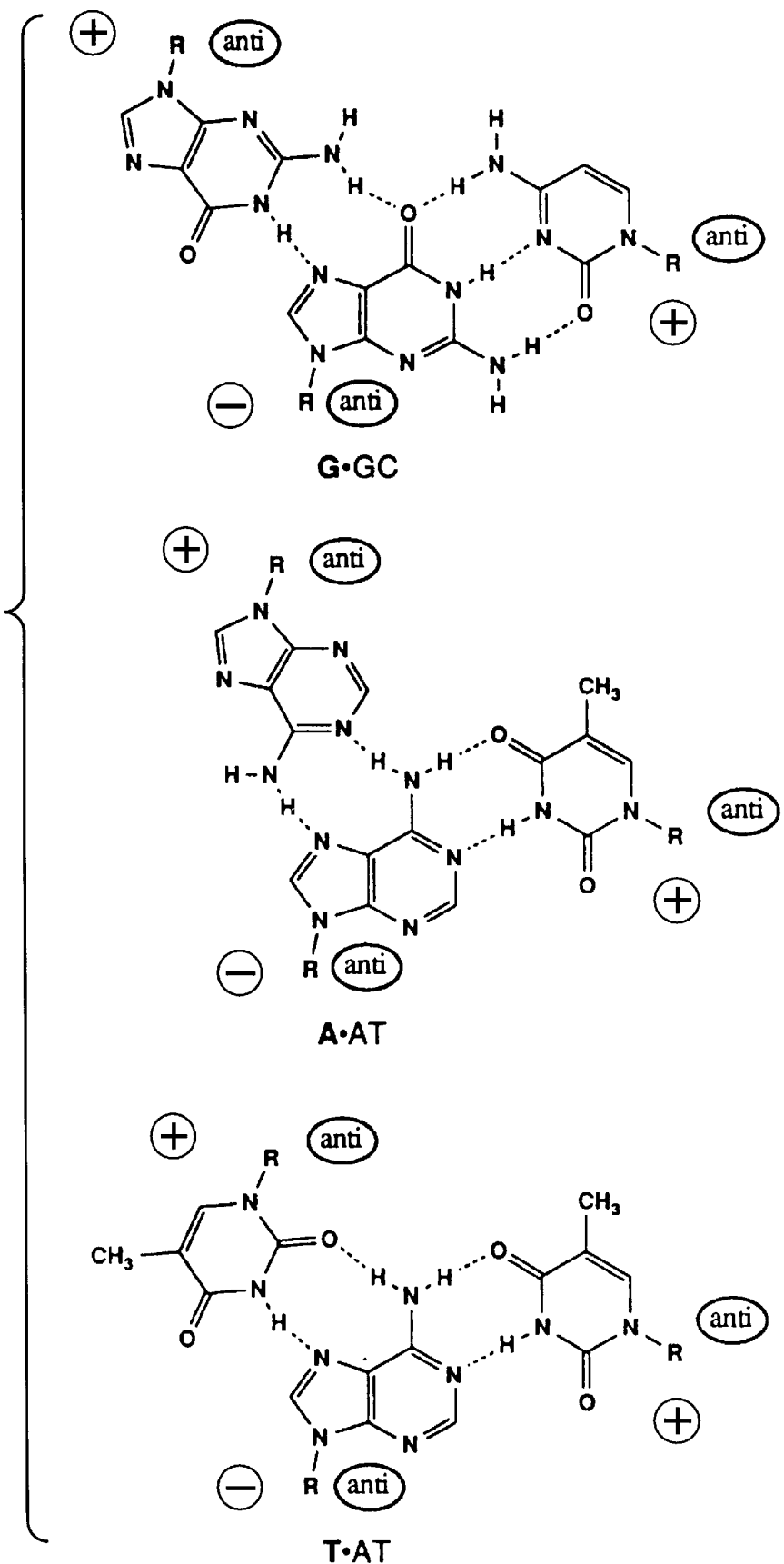
FIG._9A

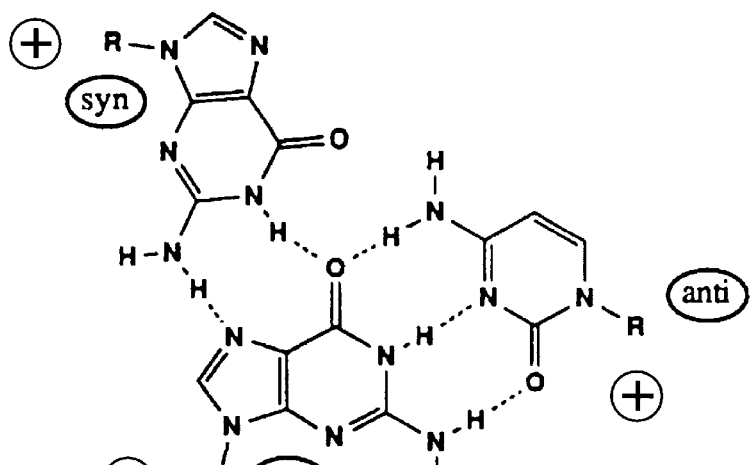
G·GC
FIG._9B
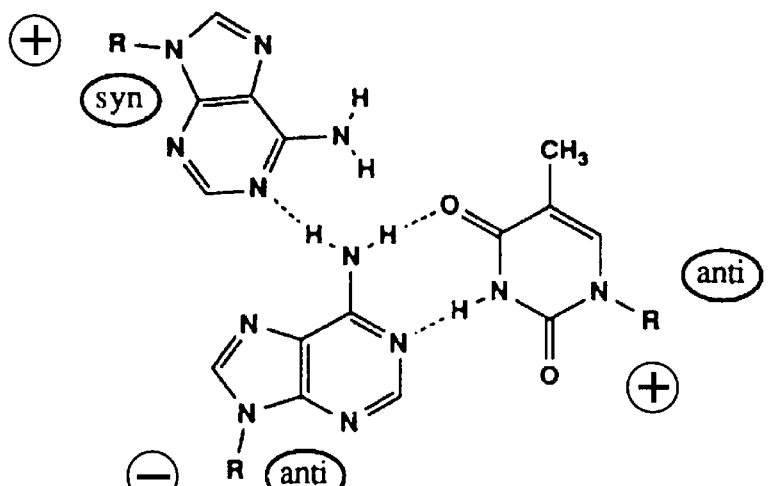
A·AT
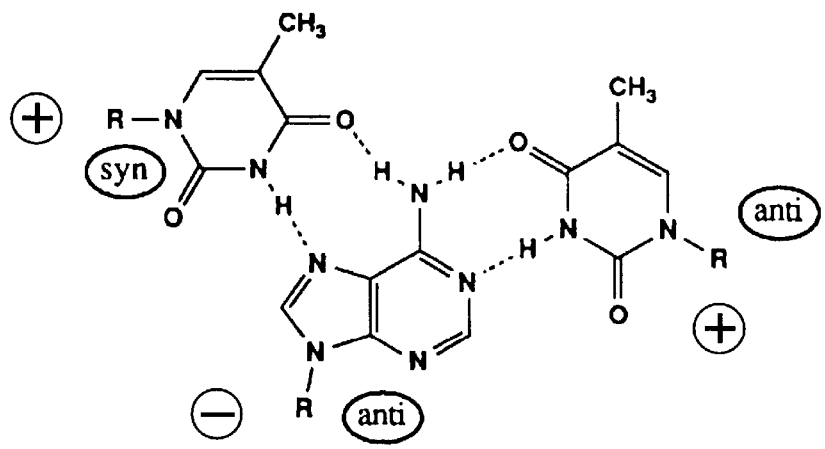
T·AT

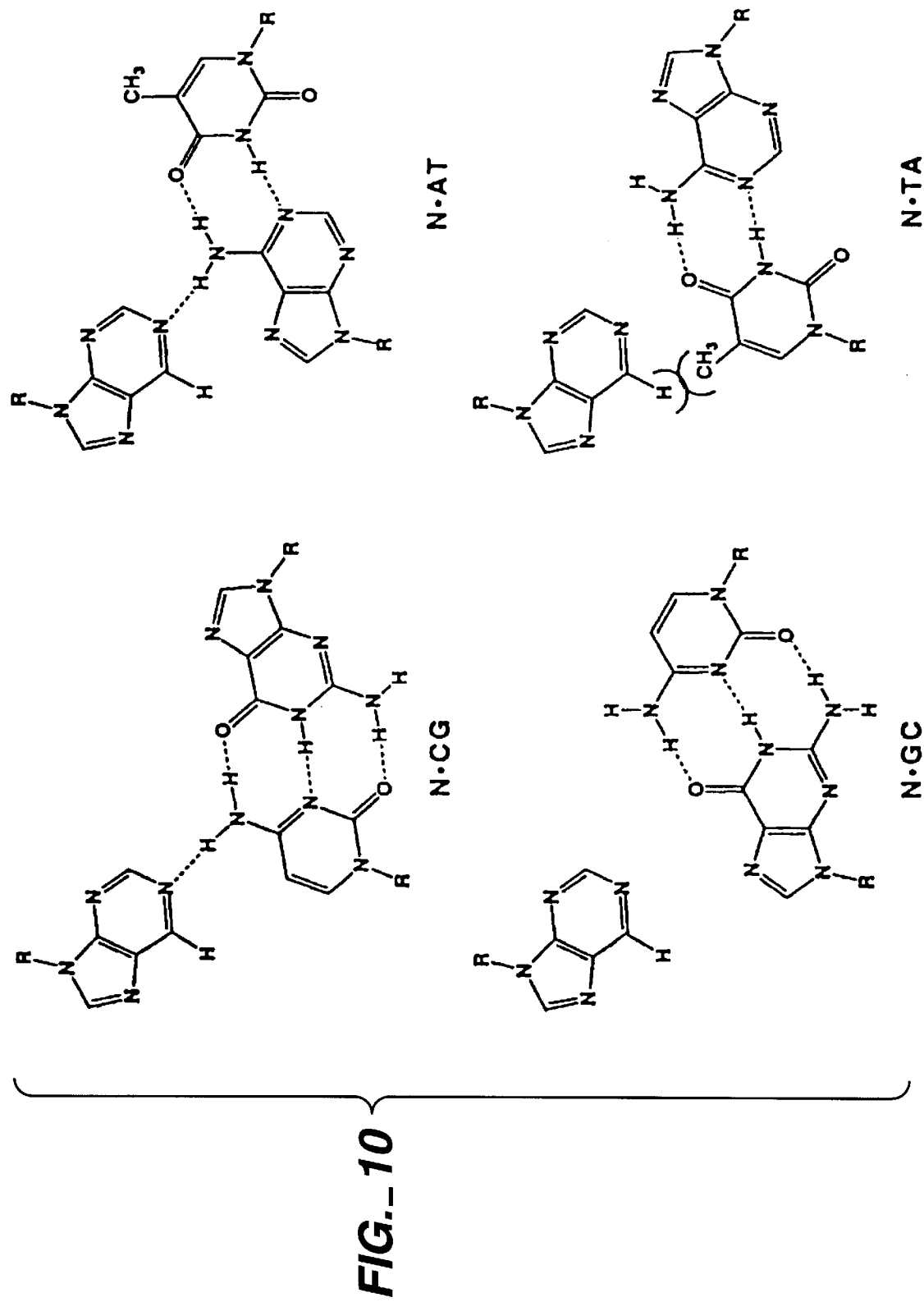
FIG._10

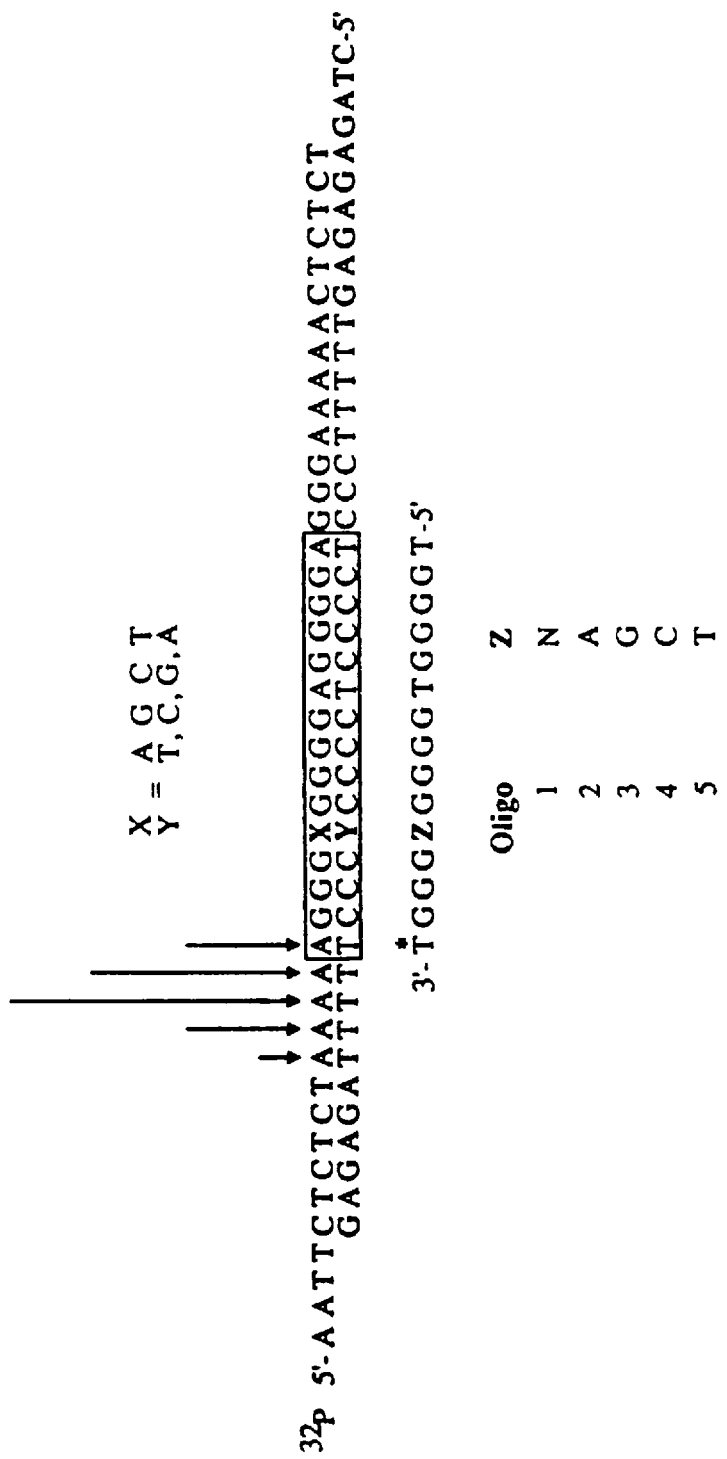
FIG._11

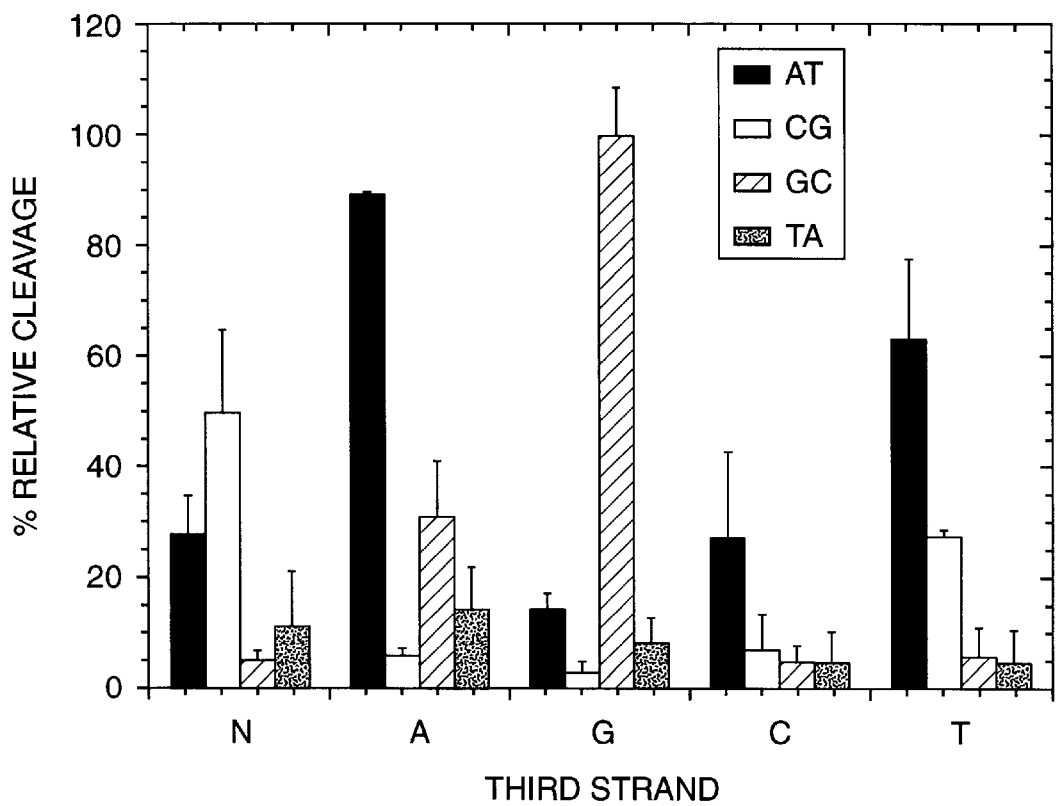
FIG._12

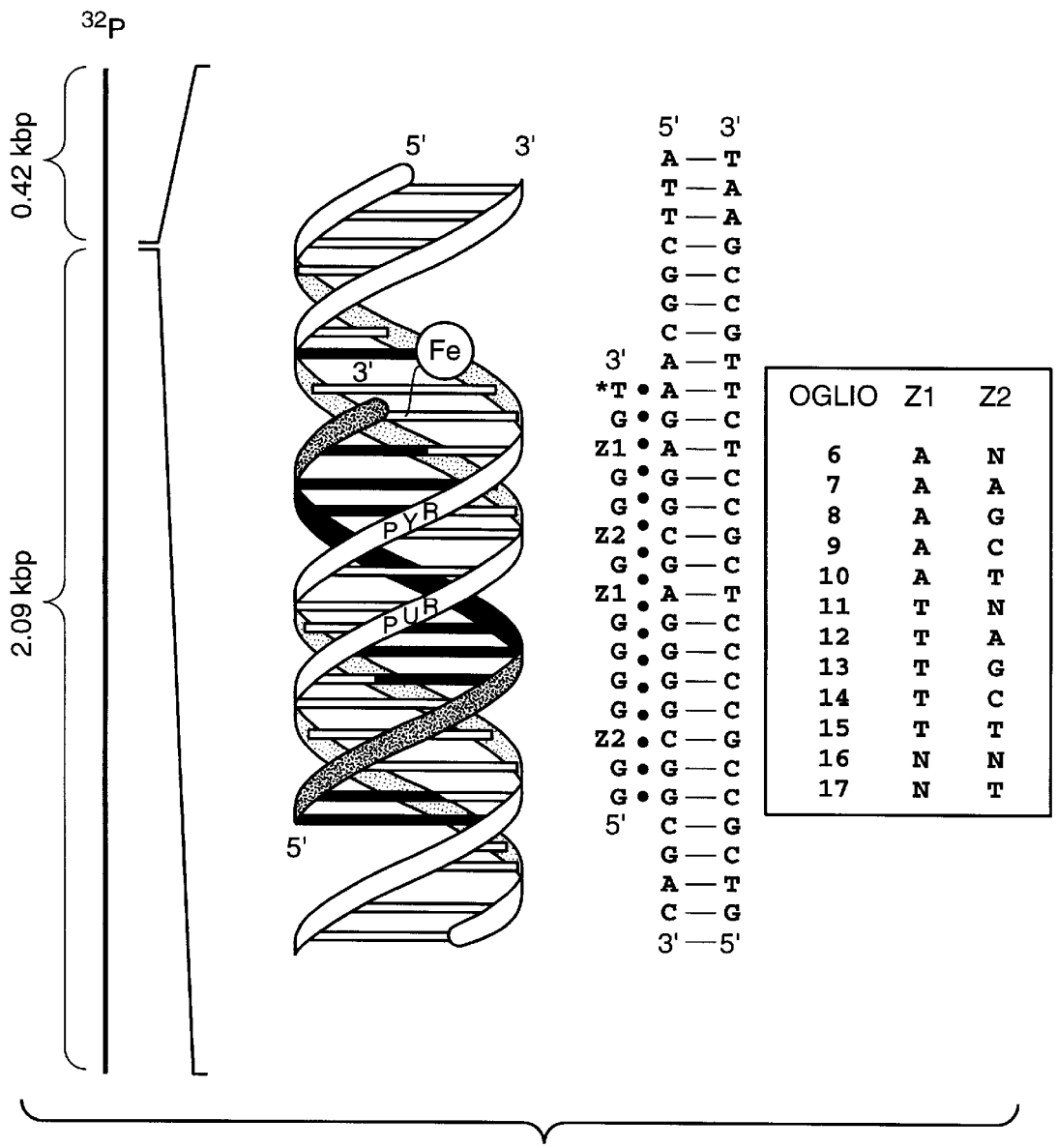
FIG._13

TRIPLE HELICES AND PROCESSES FOR MAKING SAME

This is a continuation of U.S. patent application Ser. No. 07/850,503, filed 13 Mar. 1992, abandoned, which is a continuation-in-part of U.S. patent application Ser. No. 07/115,922, filed 30 Oct. 1987, abandoned, both of which are expressly incorporated herein by reference.

FIELD OF THE INVENTION

This invention relates to the use of oligonucleotide probes for sequence-specific recognition of double-helical nucleic acids through formation of triple helices.

BACKGROUND OF THE INVENTION

The sequence-specific cleavage of double-helical deoxyribonucleic acid (hereafter "DNA") by naturally occurring restriction endonucleases is essential for many techniques in molecular biology, including gene isolation, DNA sequence determination, chromosome analysis, gene isolation and recombinant DNA manipulations. Other applications include the use of such endonucleases as diagnostic reagents to detect aberrant DNA sequences.

The usefulness of DNA cleavage by these naturally recurring restriction enzymes is limited. The binding site sizes of naturally occurring restriction enzymes are typically in the range of four to eight base pairs, and hence their sequence specificities may be inadequate for mapping genomes ($10^5$–$10^7$ base pairs) over very large distances. For unique recognition of DNA in the $10^5$–$10^7$ base pair range, sequence specificities at the 8–15 base pair level must be obtained. In addition, there are a limited number of known restriction endonucleases. Thus, they cannot be used to specifically recognize a particular piece of DNA (or RNA) unless that piece of DNA contains the specific nucleic acid sequences recognized by particular endonuclease. With the advent of pulsed field gel electrophoresis, separation of large (up to at least one million base pair) pieces of DNA is now possible. The design and synthesis of molecules that are capable of recognizing a specific sequence in double-stranded nucleic acids not otherwise detectable by natural restriction enzymes is clearly desirable as valuable tools for further research, diagnostics, and therapeutic.

Synthetic sequence-specific binding moieties for double-helical DNA that have been studied are typically coupled analogs of natural products (Dervan, P. D., *Science* 232:464 (1986)), transition metal complexes (Barton, J. K., *Science* 233:727 (1986)), and peptide fragments derived from DNA binding proteins (Sluka, J. et al., *Science*, in press). Additionally, methidiumpropyl-EDTA (hereafter "MPE"), which contains the metal chelator ethylenediaminetetraacetic acid ("EDTA") attached to the DNA intercalator methidium, has been shown to cleave double-helical DNA efficiently in a reaction dependent on ferrous iron (Fe(II)) and dioxygen ($O_2$). This mechanism is thought to occur by binding in the minor groove of the right-handed DNA helix. Addition of reducing agents such as dithiothreitol (hereafter "DTT") increases the efficiency of DNA cleavage, as reported by Hertzberg and Dervan, *J. Am. Chem. Soc.* 104:313–315 (1982); and Hertzberg and Dervan, *Biochemistry* 23:3934 (1984). MPE-Fe(II) cleaves DNA in a relatively non-sequence specific manner, and with significantly lower sequence specificity than the enzyme DNAseI, and therefore is useful in experiments to identify binding locations of small molecules such as antibiotics, other drugs, and proteins on DNA, Hertzberg and Dervan, *Biochemistry*, supra.

The most sequence-specific molecules characterized so far, with regard to the natural product analog approach is bis(EDTA-distamycin) fumaramide which binds in the minor grove and cleaves at sites containing nine contiguous A.T base-pairs (Youngquist and Dervan, *J. Am. Chem. Soc.* 107:5528 (1985)). A synthetic peptide containing 32 residues from the DNA binding domain of Hin protein with EDTA at the amino-terminus binds and cleaves at the 13 bp Hin site (Bruist, et al., *Science* 235:777 (1987); Sluka, et al., supra). Another known DNA cleaving function involves the attachment of a DNA-cleaving moiety such as a ethylenediaminetetraacetic acid-iron complex (hereafter "EDTA-Fe (II)"), to a DNA binding molecule which cleaves the DNA backbone by oxidation of the deoxyribose with a short-lived diffusible hydroxyl radical (Hertzberg and Dervan, *Biochemistry*, supra). The fact that the hydroxyl radical is a relatively non-specific cleaving species is useful when studying recognition, because the cleavage specificity is due to the binding moiety alone, not some combination of cleavage specificity superimposed on binding specificity.

Despite this progress, the current understanding of molecular recognition of DNA is still sufficiently primitive that the elucidation of chemical principles involved in creating specificity in sequence recognition at the ≧15 base pair level has been slow in development in comparison to the interest in the field for mapping large genomes.

Recognition of single-stranded nucleic acids by nucleic acid-hybridization probes consisting of sequences of DNA or RNA are well known in the art. Typically, to construct a DNA hybridization probe, selected target DNA is obtained as a single-strand and copies of a portion of the strand are synthesized in the laboratory and labeled using radioactive isotopes, fluorescing molecules, photolytic dyes or enzymes that react with a substrate to produce a color change. When exposed to complementary strands of target DNA, the labeled DNA probe binds to (hybridizes) its complementary single-stranded DNA sequence. The label on the probe is then detected and the DNA of interest is thus located. Probes may similarly be used to target RNA sequences. DNA probes are currently well known in the art for locating and selecting genes of known sequence, and in the diagnosis and chemotherapy of genetic disorders and diseases.

Oligonucleotides (polynucleotides containing between 10 and 50 bases) equipped with a DNA cleaving moiety have been described which produce sequence-specific cleavage of single-stranded DNA. Examples of such moieties include oligonucleotide-EDTA-Fe hybridization probes ("DNA-EDTA") which cleaves the complementary single strand sequence (Dreyer and Dervan, *Proc. Natl. Acad. Sci. USA* 82:968 (1985); Chu and Orgel, *Proc. Natl. Acad. Sci. USA* 82:963 (1985)). Such probes are disclosed in U.S. Pat. No. 4,795,700.

In addition to double- and single-stranded configurations, it is also well known in the art that triplexes of nucleic acids naturally exist (Howard, et al., *Biochem. Biophys. Res. Commun.* 17:93 (1964)). Poly(U) and poly(A) were found to form a stable 2:1 complex in the presence of $MgCl_2$. After this, several triple-stranded structures were discovered (Michelson, et al., *Prog. Nucl. Acid Res. Mol. Biol.* 6:83 (1967); Felsenfeld and Miles, *Annu. Rev. Biochem.* 36:407 (1967)). Poly(C) forms a triple-stranded complex at pH 6.2 with guanineoligoribonucleotides. One of the pyrimidine strands is apparently in the protonated form (Howard, et al., supra). In principle, isomorphous base triplets (T-A-T and C-G-C$^+$) can be formed between any homopyrimidine-homopurine duplex and a corresponding homopyrimidine strand (Miller and Sobell, *Proc. Natl. Acad. Sci. USA*

55:1201 (1966); Morgan and Wells, *J. Mol. Biol.* 37:63 (1968); Lee, et al., *Nucl. Acids Res.* 6:3073 (1979)). The DNA-duplex poly(dTdC)-poly(dG-dA) associates with poly (U-C) or poly(dTdC) below pH 6 in the presence of $MgCl_2$ to afford a triple-stranded complex. Several investigators have proposed an anti-parallel orientation of the two polypyrimidine strands based on an anti conformation of the bases, ibid. X-ray defraction patterns of triple-stranded fibers (poly (A)-2poly(U) and poly(dA)-2poly-(dT)) supports this hypothesis (Arnott and Bond, *Nature New Biology* 244:99 1973); Arnott and Selsing, *J. Mol. Biol.* 85:509 (1974); and Arnott, et al., *Nucl. Acids Res.* 3:2459 (1976)), and suggested an A'-RNA-like conformation of the two Watson-Crick base paired strands with the third strand in the same conformation, bound parallel to the homopurine strand of the duplex by Hoogsteen-hydrogen bonds (Hoogsteen, *Acta Cry St.* 12:822 (1959)). The twelve-fold helix with dislocation of the axis by almost three angstroms, the C3'-endo sugar puckering and small base-tilts result in a large and deep major groove that is capable of accommodating the third strand (Saenger, *Principles of Nucleic Acid Structure*, edited by C. R. Cantor, Springer-Verlag, New York, Inc. (1984)).

Although triple-stranded structures of polynucleotides were discovered decades ago, the biological significance has remained obscure. Such triplexes were proposed to be involved in processes such as regulation of gene expression, maintenance of folded chromosome conformations, chromosome condensation during mitosis, and induction of local conformational changes in B-DNA (Morgan, *Trends Biochem. Sci.* 4:N244 (1979); Hopkins, *Comments Mol. Cell Biophys.* 2:133 (1984); Minton, *J. Path.* 2:135 (1985)).

The above-described methods for sequence-specific DNA recognition and cleavage have been limited to single-stranded DNA hybridization probes, to natural or synthetic restriction endonucleases, and to those molecules which recognize sequences of DNA directly such as antibiotics, and DNA intercalators such as methidium.

SUMMARY OF THE INVENTION

Based upon the above described limitations in the recognition of specific sequences in nucleic acids, it an object herein to provide compositions and methods to detect target sequences within large double-helical nucleic acids without the need to denature such double-helical molecules.

In accordance with these and other objects, the present invention includes triple helices and synthetic oligonucleotides and methods using such oligonucleotides to form triple helices.

In one aspect, the invention provides triple helices comprising a large double-helical nucleic acid and an oligonucleotide bound to a target sequence within the double-helical nucleic acid. In specific embodiments, the target sequence comprises a purine-rich sequence on one of the strands of the double-helical nucleic acid. The triple helix formed contains the oligonucleotide bound in either a parallel or antiparallel orientation to the purine-rich target sequence depending upon the nucleotide sequences used in the oligonucleotide.

A parallel orientation occurs when the oligonucleotide is a pyrimidine-rich oligonucleotide. In particular, the pyrimidine-rich oligonucleotide contains a thymine containing nucleotide (T) when the nucleotide at the complementary position in the purine-rich target sequence is an adenosine containing nucleotide (A) and a cytosine containing nucleotide (C) when the nucleotide at the complementary position in the purine-rich target sequence is a guanine containing nucleotide (G).

An antiparallel orientation occurs when a purine-rich oligonucleotide is used. In particular, antiparallel orientation is obtained when the purine-rich oligonucleotide contains a guanine containing nucleotide (G) when the nucleotide at the complementary position in the purine-rich target sequence is a guanine containing nucleotide (G) and an adenosine containing nucleotide (A) when the nucleotide at the complementary position in the purine-rich target sequence is an adenosine containing nucleotide (A).

The invention also includes synthetic triple helix forming oligonucleotides capable of binding in an antiparallel orientation to a purine-rich target sequence in a large double-helical nucleic acid. Such triple helix forming oligonucleotides contain a G when the nucleotide in the complementary position of the purine-rich target sequence is G, a T or A when the nucleotide in the complementary position in the purine-rich target sequence is an A and the nucleotide nebularine when the complementary position in the purine-rich target sequence is C.

The oligonucleotide of the triple helices and the synthetic triple helix forming oligonucleotide can optionally contain in addition a nucleotide to which is attached at least one moiety. Such a moiety can be a detection moiety so as to permit detection of triple helix formation, a cleaving moiety capable of cleaving the double-helical nucleic acid to localize the site of triple helix formation or a therapeutic agent wherein triple helix formation targets the action of the therapeutic agent.

In addition, the invention includes processes for forming the above triple helices wherein an oligonucleotide capable of forming a triple helix is contacted with a large double-helical nucleic acid to form a triple helix. The orientation of the oligonucleotide in the triple helices formed by such methods can be in a parallel or antiparallel orientation to a purine-rich target sequence in the double-helical nucleic acid depending on the composition of the target sequence and the oligonucleotide used.

The accompanying drawings, which are incorporated in and constitute a part of the specification, illustrate some of the embodiments of the invention and, together with the description, serve to explain the principles of the invention.

BRIEF DESCRIPTION OF THE DRAWINGS

FIG. 1 depicts the bonding of two Watson-Crick base pairs, and also the bonding of isomorphous base triplets of TAT and C+GC.

FIG. 2 is a schematic representation of the cleavage of double-helical DNA by a triple helix-forming DNA-EDTA-Fe oligonucleotide, and the generation of a localized hydroxyl radical.

FIG. 3A is an autoradiogram showing the cleavage products of a double-stranded DNA containing $(dA-dT)_{15}$ after exposure to oligonucleotide DNA-EDTA probes 1–3 as analyzed by Maxam-Gilbert sequencing methods.

FIG. 3B shows the nucleotide sequence of oligonucleotide DNA-EDTA probes 1–3. This Figure also presents histograms of the DNA cleavage patterns derived by densitometry of the autoradiogram of FIG. 3A (lanes 3–5 and 8–10).

FIG. 4A is an autoradiogram showing the cleavage products of a 628 bp EcoRI/BgIl restriction fragment of plasmid pDMAG10 after exposure to oligonucleotide DNA-EDTA probes 4–9, as analyzed by Maxam-Gilbert sequencing methods.

FIG. 4B shows the nucleotide sequence of oligonucleotide DNA-EDTA probes 4–9. This figure also represents histograms of the DNA cleavage patterns derived by densitometry of the autoradiogram of FIG. 4A from the cleavage of the restriction fragment with oligonucleotide DNA-EDTA probes 4 and 9.

FIG. 5A is a bar graph presenting the absolute cleavage efficiencies obtained with oligonucleotide DNA-EDTA probe 4 under various conditions.

FIG. 5B is a bar graph presenting relative cleavage efficiencies obtained with oligonucleotide DNA-EDTA probes 4–8 at three temperatures.

FIG. 6 is an autoradiogram showing the cleavage products of plasmid pDMAG10 after exposure to oligonucleotide DNA-EDTA probe 9 under various conditions, as analyzed on a nondenaturing agarose gel.

FIG. 7 (left) is a resolution cleavage pattern from FIG. 6, a simplified schematic model depicting a triple helix complex with the Hoogsteen bound oligonucleotide DNA-EDTA probe 9 at one unique site within the 4.06 kb of plasmid DNA. The pyrimidine-rich oligonucleotide probe is bound in a parallel orientation to the purine-rich target sequence on one of the strands of the double-helical nucleic acid.

FIG. 8A is an autoradiogram of a sequencing gel showing the dependence of cleavage efficiency on the sequence composition of purine-rich oligonucleotides capable of forming triple helices with an antiparallel orientation to a purine-rich target sequence. The site of triple helix formation is shown on the left. The actual sequence of the double-helical DNA and oligonucleotide within and flanking the triple helix site is shown immediately to the right of the sequencing gel. In FIG. 8B, the triple helix forming oligonucleotide is oriented in the antiparallel orientation to the purine-rich target sequence in the double-helical DNA. A ribbon model showing the local triple helical complex with the oligonucleotide in antiparallel orientation is shown immediately to the right of the triple helix sequence.

FIG. 9A depicts models for G.GC, A.AT and T.AT triplets within a triple helix motif where the third strand oligonucleotide is antiparallel to the purine W-C strand and the bases are in the anti-conformation. FIG. 9B depicts models for G.GC, A.AT and T.AT triplets where the third strand is antiparallel to the purine W-C strand and the bases are in the syn conformation. The plus and minus signs indicate relative polarities of the phosphatedeoxyribose backbones in FIGS. 9A and 9B.

FIG. 10 depicts the models for base triplets N.AT, N.CG, N.GC, and N.TA formed between 2'-deoxynebularine and the Watson-Crick duplex within the pur.pur.pyr triple-helix motif. All bases are depicted with anti glycosidic bonds and the phosphate-deoxyribose backbone of the third strand was positioned as to be compatible with the purine triple-helix motif.

FIG. 11 depicts the sequences of oligodeoxynucleotide-EDTA 1–5 wherein T* indicates the position of thymidine-EDTA. The oligodeoxynucleotides differ at one base position indicated in bold type to the four common natural DNA bases (A, G, C, T) and to 2'-deoxynebularine (N). Also shown are the sequences of the target double-helical DNA. The box indicates the double stranded sequence bound by oligodeoxynucleotide-EDTA.Fe(II) 1–5. The Watson-Crick base pair (AT, GC, CG, or TA) opposite the variant base in the oligodeoxynucleotide are in bold type. The height of the arrows represent the relative cleavage efficiencies at the indicated bases as determined by quantitative analysis using storage phosphor autoradiography.

FIG. 12 is a histogram depicting relative cleavage intensities (normalized) for the twenty base triplets. The values were obtained by phosphorimager quantitative analysis and represent the mean +/− standard diviation of two determinations.

FIG. 13 is a ribbon model and sequence of the triple helix complex between a single site in the pULHIV EcoO1091-SspI restriction fragment and oligodeoxynucleotide-EDTA 6–17. The purine oligodeoxynucleotide with EDTA.Fe(II) at the 3' termini is located near the center of the major groove of the double-helical DNA antiparallel to the purine strand. The target site is located 0.42 kbp from the $^{32}$P radiolabeled end of the restriction fragment.

DETAILED DESCRIPTION OF THE INVENTION

As used herein, a "triple helix" is defined as a double-helical nucleic acid with an oligonucleotide bound to a target sequence within the double-helical nucleic acid. The double-helical nucleic acid can be any double-stranded nucleic acid including double-stranded DNA, double-stranded RNA and mixed duplexes between DNA and RNA. Such double-helical nucleic acids preferably have a length greater than 500 bp, more preferably greater than 1 kb and most preferably greater than about 5 kb. In many applications, the double-helical nucleic acid comprises genomic DNA from procaryotic or eucaryotic sources. When such genomic DNA is used it can comprise fragmented DNA, DNA digested with restriction endonucleases, or DNA cleaved according to the methods of the invention or as described by Strobel and Dervan, *Nature* 350:172–174 (1991), and Strobel, et al., *Science* 254:1639–1642 (1991). While such portions of genomic DNA are useful in practicing the invention, an important aspect of the invention is the formation of triple helices with chromosomal DNA either in situ or in vivo. When genomic DNA is utilized, the oligonucleotides used to form triple helices are particularly useful to detect the presence or absence of specific sequences within the genomic DNA for diagnostic and therapeutic purposes. Further, such genomic triple helices can be used in conjunction with the protocols of Strobel and Dervan, and Strobel, et al., supra, for limited enzymatic cleavage of genomic DNA.

For example, numerous genetic diseases have been identified wherein a gene has been modified by way of substitution, insertion or deletion of one or more nucleotides to cause an inheritable recessive or dominant genotype. In addition, a number of polymorphisms, including restriction fragment length polymorphisms and other unique sequences, have been found to be associated with as yet unidentified inheritable gene defects such as these associated with autoimmune diseases and the like. Appropriate synthetic oligonucleotides can be used in the methods of the invention to detect such diagnostic sequences in genomic DNA (or in some cases in double-stranded cDNA derived from an appropriate tissue) as a means to diagnose the presence of one or more defective alleles for a particular disease, provided such diagnostic sequences are amenable to triple helix formation.

In addition, the triple helices of the invention have an enormous potential for the treatment of various disease states. For example, oligonucleotides can be selected which specifically bind to pathogenic double-stranded DNA including specific sequences required by pathogenic bacteria or viruses for replication or virulence. Alternatively, the oligonucleotide can be chosen to target a unique sequence of the pathogen which is not found in the genome of the pathogen's host. Such an oligonucleotide further includes a therapeutic agent which selectively kills the pathogen or a cell containing it based upon the selective specificity of the oligonucleotide for the pathogenic DNA.

Another important potential therapeutic application of triple helix technology involves cancer treatment by way of triple helix suppression of specific oncogenes including those of endogenous or viral origin. When so used, one or more oncogenes identified with a particular tumor type are used as targets for triple helix formation. Specific oligonucleotides designed for triple helix formation to suppress the expression of hyper-expressed oncogenes are designed to repress expression. Alternatively, when an activated oncogene contains unique sequences associated with such activation, oligonucleotides specific for the unique sequence and which contain a therapeutic agent can be used. Such therapeutic oligonucleotides are capable of selectively forming a triple helix with such sequences in those cancerous cells containing the activated oncogene thereby preferentially killing or repressing the cancer causing cell type.

As used herein, a "target sequence" within a double-helical nucleic acid comprises a sequence preferably greater than 10 nucleotides in length but preferably less than 20 nucleotides within the double-helical nucleic acid. The target sequence is most preferably between 11 to 18 bases. The target sequence, in general, is defined by the nucleotide sequence on one of the strands of the double-helical nucleic acid. In the preferred embodiments herein, the target sequence is defined by a purine-rich containing strand.

As used herein, a "purine-rich sequence" on one of the strands of double-helical nucleic acid is defined as a contiguous sequence wherein greater than 50% of the nucleotides of the target sequence contain a purine base. However, it is preferred that the purine-rich target sequence contain greater than 60% purine nucleotides, more preferably greater than 75% purine nucleotides, next most preferably greater than 90% purine nucleotides and most preferably 100% purine nucleotides. When such a target sequence contains greater than approximately 90% purine nucleotides, it is sometimes referred to as a purine tract or a substantially homopurine tract.

The oligonucleotides used in triple helix formation are generally of substantially the same length as the target sequence in the double-helical nucleic acid and have a sequence which permits binding of the oligonucleotide to the target sequence in either a parallel or antiparallel orientation as compared to the target sequence. In a parallel orientation, the oligonucleotide is oriented such that its 5' end is positioned at the 5' end of the target sequence and its 3' end is positioned at the 3' end of the target sequence. When oriented in an antiparallel orientation the 5' end of the oligonucleotide is positioned at the 3' end of the target sequence and the 3' end of the oligonucleotide is positioned at the 5' end of the target sequence. It is to be understood, of course, that reference to the 5' end and 3' end of the target sequence is not to be construed as the physical end of the double-helical nucleic acid but rather refers to the 5' to 3' sequence orientation in the strand containing the target sequence.

When the target sequence is a purine-rich sequence, parallel binding of the oligonucleotide occurs when the oligonucleotide is a pyrimidine-rich oligonucleotide. Antiparallel binding, however, occurs when a purine-rich oligonucleotide is used. As indicated hereinafter, the specific rules for parallel and antiparallel binding define a particular nucleotide contained within an oligonucleotide when the nucleotide at the "complementary position" in the target sequence is a specified nucleotide. This term means that when the oligonucleotide is positioned in a parallel or antiparallel orientation at a target sequence that there is a correspondence in the position of the various nucleotides in the oligonucleotide with the nucleotides contained in the target sequence. While it is believed that the oligonucleotide binding is within the major groove of a double-helical nucleic acid such as DNA and that the rules defining sequence binding have a physical basis with regard to the triplets proposed for triple helix formation, the use of such language is not to be construed as a limitation on the mechanism of triplex helix formation.

Parallel Binding to Purine-Rich Target Sequences

As indicated, parallel binding of an oligonucleotide to a purine-rich target sequence occurs when the oligonucleotide comprises a pyrimidine-rich oligonucleotide. In general, the following rules apply to the formation of triplets within the triple helix.

The pyrimidine-rich oligonucleotide contains a T when the nucleotide at the complementary position in the purine-rich target sequence is A. Further, the pyrimidine-rich oligonucleotide contains a C when the nucleotide at the complementary position in the purine-rich target sequence is G.

FIG. 1 shows typical binding of base pairs and triplets as referred to herein for parallel binding to a purine-rich target sequence according to the foregoing rules. Structure 1 of FIG. 1 shows a standard representation of Watson-Crick base pairing of nucleotide bases A (adenine) and T (thymine). Major groove 2 and minor groove 3 are shown where they would appear in an A-helical structure; B-helical structures (not shown) are also encompassed within the scope of this invention. Structure 4 of FIG. 1 shows Watson-Crick base pairing of G (guanine) and C (cytosine). Major groove 5 and minor groove 6 are indicated. Structure 7 of FIG. 1 shows isomorphous base triplets of TAT wherein the additional pyrimidine strand is bound by Hoogsteen-hydrogen bonds in the major groove to the complementary purine strand shown in Watson-Crick duplex 1. Structure 8 of FIG. 1 shows isomorphous base triplets of C+GC. The additional pyrimidine is bound as described above.

Antiparallel Binding to Purine-Rich Target Sequences

As indicated, antiparallel binding of an oligonucleotide to a purine-rich target sequence occurs when the oligonucleotide comprises a purine-rich oligonucleotide. In general, the following rules apply to formation of triplets in such a triple helix.

The purine-rich oligonucleotide contains a G when the nucleotide at the complementary position in the purine-rich target sequence is G. Such an oligonucleotide also contains an A when the nucleotide in the complementary position in the purine-rich target sequence is A.

In addition to the foregoing rules, it has been determined that the nucleotide nebularine, or its analogs (e.g., 2'-deoxynebularine), is capable of binding to the pyrimidine nucleotide C in a purine-rich target sequence. This binding occurs when the nebularine is incorporated into an oligonucleotide designed for antiparallel binding to the purine-rich, but C-containing target sequence. When nebularine is used, it can be the sole nucleotide used to pair with a C nucleotide in the target sequence. However, since T is also capable of pairing with a C nucleotide in the purine-rich target sequence, albeit in a less energetically favorable manner, the oligonucleotide can contain nebularine nucleotides alone or nebularine nucleotides in combination with the pyrimidine nucleotide T.

When one or more nebularine nucleotides are used, the following rules apply. The purine-rich oligonucleotide contains a G when the nucleotide at the complementary position of purine-rich target sequence is G. In addition, the purine-rich oligonucleotide contains an A or a T when the nucleotide at the complementary position in the purine-rich target sequence is A. However, the total T content of the triple helix forming oligonucleotide is preferably less than 40% of the oligonucleotide sequence and most preferably less than 25%. When greater amounts of T nucleotides are used in an oligonucleotide, the antiparallel orientation of the oligonucleotide to the purine-rich target strand becomes less favorable and as a consequence, a shift to a parallel orientation can occur. Thus, an oligonucleotide containing 20 nucleotides designed for antiparallel orientation to a purine-rich target sequence of 20 nucleotides preferably contains no more than 5 to 8 T nucleotides to maintain the antiparallel orientation.

Production of Triple Helix Forming Oligonucleotides

The oligonucleotides used in the invention to form triple helices can be made synthetically by well-known synthetic techniques to contain a structure corresponding to the naturally occurring polyribonucleic or polydeoxyribonucleic acids. Alternatively, the phosphoribose backbone of such oligonucleotides can be modified such that the thus formed oligonucleotide has greater chemical and/or biological stability. Biological stability of the oligonucleotide is desirable when the oligonucleotides are used in vivo for diagnostic or therapeutic uses. Such modified oligonucleotides are synthesized with a structure which is stable under physiological conditions which include enhanced resistance to nuclease degradation. Further, when used in vivo, such nucleotides preferably have a minimal length which permits targeted triple helix formation so as to facilitate the transport of the oligonucleotide across the membranes of the cytoplasm and nucleus.

In specific embodiments of this invention, a moiety is included in the triple helix forming oligonucleotide. Moieties such as a label, a therapeutic agent, or a cleavage moiety are incorporated along the length of any such oligonucleotide so as to provide precisely the detection, treatment or cleavage desired by the practitioner. Also, more than one moiety may be included in the oligonucleotide. Previously known and familiar synthesis protocols can be employed, in some cases using currently available automated technology, wherein such moieties can be incorporated into the triple helix forming oligonucleotide.

A nucleic acid-cleaving moiety can be attached to a nucleoside base during synthesis of a novel nucleoside and the so-modified nucleoside then incorporated into a selected oligonucleotide using standard procedures. This oligonucleotide containing the cleavage moiety recognizes the corresponding target sequence of a double-helical nucleic acid. For example, a metal chelator for cleaving a specific double-helical nucleic acid sequence is tethered to a triple helix forming oligonucleotide. FIG. 2 depicts oligonucleotide-directed cleavage of double-helical DNA by a triple helix forming oligonucleotide DNA-EDTA-Fe probe. One thymidine has been replaced by thymidine with the iron chelator EDTA covalently attached at C-5. Reduction of dioxygen generates a localized hydroxyl radical at this point. Alternatively, the metal chelator may be attached to a selected nucleotide located within a given oligonucleotide sequence. In the presence of dioxygen (O2), an appropriate metal ion, and a reducing agent, the DNA-chelator probe yields a strand break at the target complementary DNA sequence, cleaving one or both strands at that site.

Oligonucleotides equipped with a DNA cleaving moiety have been described which produce sequence-specific cleavage of single-stranded DNA. See, e.g., U.S. Pat. No. 4,795,700. Examples of such moieties include oligonucleotide-EDTA-Fe probes (DNA-EDTA) which cleave a complementary single strand sequence (Dreyer and Dervan, Proc. Natl. Acad. Sci. USA 82:968 (1965); and Chu and Orgel, Proc. Natl. Acad. Sci. USA 82:963 (1965)). One example of a DNA-EDTA probe is a novel nucleoside, 5'-DMT-T*-triethylester derived from deoxyuridine to which is attached the metal chelator EDTA as described in detail in U.S. Pat. No. 4,795,700. Such probes are also described in Dreyer and Dervan, Proc. Natl. Acad. Sci. USA, supra. These references disclose an EDTA-nucleoside composition incorporated into a 19-nucleotide base pair sequence of DNA complementary to a 19 bp sequence in a 167 bp restriction fragment of DNA from the plasmid pBR322. This DNA-EDTA probe was then used in the presence of the metal ion Fe(II), atmospheric dioxygen, and the reducing agent dithiothreitol (DTT) to afford specific cleavage at its complementary 9 bp complement in single-stranded plasmid DNA.

Chelators or other cleavage moieties, as well as marker labels and therapeutic agents may also be incorporated into the triple helix forming oligonucleotide of the present invention at various positions for which the chemistry for attachment at such positions is known, provided that such attachment is accomplished so as not to disrupt the hydrogen-base pair bonding between the DNA or RNA sequences during triple helix formation.

The triple helix forming oligonucleotide may be labeled in various well known ways for detection and diagnostic applications. For example, with radioactive metals such as $^{99}$Tc following the procedures of Elmalch, D. R., et al., Proc. Natl. Acad. Sci. USA 81:918 (1984) and EDTA or with fluorescent elements such as the lanthanides $Tb+^3$ or $Eu+^3$. Leung, et al., Biochem. Biophys. Res. Comm. 75:15 (1977). If a chelator is desired to be used in a cleavage moiety, other metal chelators may be used in place of EDTA such as polyamines or other chelators capable of binding Fe(II–III) or Cu(I–II). Other polyamino carboxylic metal chelators may be utilized in place of EDTA such as 1,2-diamino-cyclohexane tetraacetic acid, diethylenetriamine pentaacetic acid, ethylenediamine di-(-O-hydroxyphenol-acetic acid), and hydroxyethylene diamine triacetic acid. A metal chelator may be attached to the nucleotide probe during synthesis via a hydrocarbon-amide linkage which may consist of several carbon atoms. The specificity of the probe for the reaction site is prescribed by the nucleotide sequence within which the metal chelator or other cleavage moiety is attached. The moiety can be incorporated into polydeoxyribonucleotides or polyribonucleotides of any desired length and sequenced using routine phosphoramidite or phosphotriester procedures.

One convenient synthesis of DNA-EDTA probes involves the incorporation of a modified thymidine into an oligonucleotide by chemical methods. This approach allows for automated synthesis and affords control over the precise location of the EDTA moiety at any thymidine position in the oligonucleotide strand, Felsenfeld, et al., supra.

In an embodiment of this invention, bifunctional DNA-EDTA probes are used for recognition and cleavage of a double-stranded nucleic acid. These probes allow triple helix formation at a discrete location to be mapped on large DNA using gel electrophoresis. An important part of the present invention involves the development of preferred assay conditions for measuring formation and cleavage of the triple helix. This will be discussed in more detail in Example 2 below. However, the preferred general conditions for the cleavage reactions are as follows: approximately 100 nM in bp radio labeled restriction fragment (approximately 10,000 cpm), 25 nM tris/acetate, pH 7.0, 1 nM spermine, (MY), 100 nM NaCl, 100 umolar in vp sonicated, deproteinized cath-thimus DNA, 20 volume-percent ethyleneglycol, 1 ymolar DNAEDTA probe, 25 umolar Fe(II) and 2 nM DTT. The cleavage reactions were run for approximately 16 hours at 0°–25° C. These conditions may be varied without departing from the scope of this invention.

As described in the examples below, the affinity cleaving method utilizing DNA, EDTA and known in the art allows the effect of reaction conditions, probe length, and single base mismatches on triple helix formation to be analyzed on high resolution sequencing gels. Precise methods for quantitation and measurement and determination of the presence and orientation of triple helices is set out in more detail in the Examples below.

As will be seen in the Examples, the directional orientation of the third strand as well as the identity of the grooves in right-handed DNA-helix occupied by the bound DNA-EDTA probe can be analyzed by high resolution gel electrophoresis (FIG. 2). Additionally, the location of triple helices within large pieces of DNA can be mapped by double-strand breaks analyzed by nondenaturing agarose gel electrophoresis.

Synthesis and the preparation of necessary and desired component parts of the probes of the present invention, and their assembly is believed to be within the duties and tasks performed by those with ordinary skill in the art and, as such, are capable of being performed without undue experimentation.

The oligonucleotide probes of the present invention are not limited to the production of sequence-specific cleavage of double-stranded DNA by triple helix formation, but may also be utilized as diagnostic agents when a radioisotope labeled, fluorescing, or otherwise detectable metal ion is attached to the probe. The probes of the present invention may also be used as target-specific therapeutics with the attachment of an "artificial" or natural gene repressor or other effective agent to the oligonucleotide.

the following is presented by way of example, and not to be construed as a limitation to the scope of the appended claims.

EXAMPLE 1

Determination of Parallel Orientation and Groove Location of Hoogsteen Strand Binding Watson-Crick DNA Nine homopyrimidine DNA probes, 11–15 nucleotides in length, described in more detail below, each containing a single thymidine with EDTA covalently attached at C-5 (labeled T*), were synthesized for binding and cleavage studies with two different duplexed target DNA's.

Generally, unless specifically controverted below, the following definitions apply: DMT refers to 4,4-dimethoxytrityl; DTT refers to dithiothreitol; DNA-EDTA 1–9, the probes examined below, refers to oligodeoxyribonucleotides with an EDTA-modified thymidine at positions 1, 5, or 8; Spermine indicates spermine-4-HCl (Aldrich, 98× pure) which was dissolved in water and then pH adjusted with NaOH to 7.4; TBE-buffer includes 0.89 nM TRIS (meaning TRIS(hydroxymethyl)aminomethane), 0.89 mM Boric acid, and 1 mM EDTA-disodium salt; Fe(II) refers to $Fe(NH_4)_2(SO_4)_2 \cdot 6H_2O$. Aqueous solutions of DTT and Fe(II) were freshly prepared before use.

A double-stranded DNA was examined that contains $(dA-dT)_{13}$ as a target sequence which could, in principle, bind a $d(T)_{13}$ oligonucleotide in parallel or antiparallel orientation. A 30-base pair duplex of DNA containing $(dA-dT)_{13}$ with all purines on one strand was labeled separately at the 5' end of each strand. This was allowed to incubate with $d(T)_{13}$-EDTA probes 1 to 3 (shown in FIG. 3B) with the thymidine-EDTA located at oligonucleotide positions 8, 5, and 1, from the 3'-end, respectively. The $^{32}$P-labeled DNA was dissolved in buffer containing calf-thymus DNA, NaCl, TRIS, spermine and ethylene glycol and was mixed with the DNA-EDTA-FeII) probes, previously equilibrated with Fe(II) for 1 minute. After incubation at 0° C. for 10 minutes, the reactions were initiated by addition of an aqueous solution of DTT, such that the final concentrations were 10 mM TRIS/HCl (pH 7.4), 1 mM spermine, 100 mM NaCl, 40 vol-ethylene glycol, 100 $\mu$M (bp) of calf thymus DNA, 0.67 $\mu$M DNA-EDTA probe, 25 $\mu$M Fe(II) and 1 mM DTT. The pH values are not corrected for temperature or different ethylene glycol percentage and are given for the ten-fold concentrated buffer solution at 25° C. The cleavage reactions were allowed to proceed for 15 hours at 0° C. and then stopped by freezing and lyophilization. The resulting cleavage products were separated by electrophoresis on a denaturing 20 percent polyacrylamide gel and visualized by autoradiography (FIG. 3A).

FIG. 3A shows an autoradiogram of the 20 percent Maxam-Gilbert sequencing gel. Lanes 1 to 5 contain 5'-End-labeled $d(A_5T_{15}G_{10})$; lanes 6 to 10 contain 5'-End-labeled $d(C_{10}A_{15}T_5)$. The Maxam-Gilbert G+A sequencing reactions used for lanes 1 and 6 are disclosed in Maniatis Ct *Molecular Cloning, A Laboratory Manual*, Cold Spring Harbor Laboratory (1982), and Maxam and Gilbert, *Methods Enzymol.* 65:499 (1987). Controls in lanes 2 and 7 showing the two 5'-labeled 30-bp DNA standards were obtained by treatment according to the cleavage reactions in the absence of oligonucleotide DNA-EDTA-Fe probes. Lanes 3 to 5 and 8 to 10 are the DNA cleavage products in the presence of oligonucleotide DNA-EDTA-Fe probes 1 to 3, approximately 0.5 $\mu$M (bp) 5'-$^{32}$P-labeled DNA, (approximately 10,000 cpm), 10 mM TRIS/HCl, pH 7.4, 1 mM spermine, 100 mM NaCl, 100 $\mu$M (bp) sonicated, deproteinized calf thymus DNA, 40 percent by volume ethylene glycol, 0.67 $\mu$M oligonucleotide probe, 25 yM Fe(II) and 1 mM DTT; incubated for 15 hours at 0° C. Lanes 3 and 8 contain oligonucleotide DNA-EDTA-Fe 1, lanes 4 and 9 contain DNA-EDTA-Fe 2, lanes 5 and 10 are oligonucleotide DNA-EDTA-Fe 3.

On the $d(T)_{15}$ strand of the Watson-Crick duplex, one major cleavage site is observed for each oligonucleotide DNA-EDTA probe 1–3 with the maximum cleavage site shifted to the 5'-side of T*. The location of the cleavage patterns on Watson-Crick DNA produced by the oligonucleotide probes 1–3 with respect to the position of T* reveal the orientation of the DNA-EDTA probe on the duplex DNA (FIG. 3B).

FIG. 3B shows the oligonucleotide $(T)_{15}$-EDTA probes 1–3, where T* is the position of the thymidine-EDTA. Also shown are histograms of the DNA cleavage patterns for these probes, derived by densitometry of the autoradiogram shown in FIG. 3A (lanes 3–5 and 8–10). The heights of the arrows represent the relative cleavage intensities at the indicated bases. Arrows are shown if the cleavage intensity at a particular nucleotide was greater than 5% when compared to that of the nucleotide cleaved the most efficiently. The box in each histogram indicates the double-stranded sequence which is bound by the oligonucleotide DNA-EDTA-Fe(II) probes 1–3. The Watson-Crick base-pair to which T* is Hoogsteen hydrogen bonded in the triple-strand helix is shaded.

As seen from the orientations, the pyrimidine-rich EDTA oligonucleotide binds parallel to the purine-rich and anti-parallel to the pyrimidine-rich strands of the Watson-Crick double-helical DNA. These observations rule out strand displacement (D-loop) as the mode of binding. The asymmetry of the cleavage patterns on opposite strands of DNA reveals the identity of the groove in right handed DNA occupied by the oligonucleotide DNA-EDTA-Fe probes. An asymmetric cleavage pattern with maximal cleavage shifted to the 5' or 3' side on opposite strands corresponds to the diffusible hydroxyl radical being generated in the major or minor groove, respectively. The cleavage patterns shown in FIG. 3B reveal that the oligonucleotide DNA-EDTA-Fe(II) probe is located in the major groove of the Watson-Crick DNA.

Pyrimidine-rich oligonucleotide probes 1 and 2 which bear the EDTA at an internal base position cleave exclusively the pyrimidine-rich strand of the DNA containing the target sequence. A model of the triple helix between these pyrimidine-rich oligonucleotide EDTA-Fe(II) probes and the double-helical DNA (not shown) reveals that the purine-rich Watson-Crick strand in the triple helix is protected from the hydroxyl radical by the sugar-phosphate backbones of the Hoogsteen-paired strand. In effect there are now three grooves in the triple helix and EDTA-Fe is exposed to only one groove (FIG. 1). The nucleotides 3 to 4 bases on the 5'-side of T* in the right-handed triple helix are proximal to the EDTA-Fe(II) and are therefore expected to be cleaved most efficiently. Oligonucleotide DNA-EDTA-Fe(II) 3, which carries the cleaving moiety at the 5'-end, should form a triplex with no flanking nucleotides on the 5'-side of T*. A pyrimidine-rich oligonucleotide probe with the cleaving function at the 5'-end should generate cleavage on both strands. Indeed, the oligonucleotide d(T)$_{15}$-EDTA-Fe(II) 3, carrying the EDTA at the 5' end, cleaves both strands of the target duplex DNA (FIG. 3B).

EXAMPLE 2

Specific Cleavage of a DNA Restriction Fragment and Determination of Assay Conditions This example illustrates two important aspects of the present invention. In the first part, it is shown that an unsymmetrical mixed oligonucleotide probe can precisely recognize a purine-rich target sequence within double-helical DNA having a length 50-fold greater than the oligonucleotide probe. In this example, restriction fragments with mixed bases are used which vary in length, have single mismatches with the known target, and vary in the positions of the EDTA (FIG. 4B).

In the second part preferred assay conditions are determined, as well as the effect of varying those conditions with probes oligonucleotide of 11–15 bp in length.

Specific Cleavage of a DNA Restriction Fragment

Cleavage by triple helix formation with oligonucleotide DNA-EDTA-Fe(II) probes 4–9 was examined on a restriction fragment 628 base pairs in length that contained the sequence d(AAAAAGAGAGAGAGA). This sequence was obtained from plasmid pDMAG10 which was a gift from D. Mendel, who constructed it by inserting the d(AAAAAGAGAGAGAGA) containing duplex in the large BamHI-HindIII restriction fragment of pBR322 (Mendel and Dervan, Proc. Natl. Acad. Sci. USA 84:910 (1987)). A single site labeled 628 bp EcoRI-BglI restriction fragment containing the purine-rich target sequence was obtained by linearizing pDMAG10 with EcoRI, labeling with $^{32}$P (Van Dyke and Dervan, Science 225:1122 (1984)), and cleaving with BglI. This sequence represents a mixed purine-rich target which is located 47 nucleotides from the 3'-(and 5')$^{32}$P-label of the DNA fragment. The concentration of the single stranded oligodeoxynucleotides were determined using the following epsilon values (260 mm) for each base: 15400(A), 11700(G), 7300(C) and 8800(T).

FIG. 4A shows an autoradiogram of the 8 percent Maxam-Gilbert high-resolution polyacrylamide sequencing gel run on oligonucleotide probes 4–9. The EcoRI/BglI restriction fragment of plasmid pDMAG10 is labeled at the 3' end with $^{32}$P. The Maxam-Gilbert GNA sequencing reactions described in the previous example were used here for lane 20. In general, the cleavage reactions were carried out as follows: a mixture of oligonucleotide DNA-EDTA probe (1 μM) and Fe(II) (25 μM) was combined with the $^{32}$P-labeled restriction fragment (approximately 100 μM (bp)) in a solution of calf-thymus DNA (100 μM (bp)), NaCl (100 mM), TRIS/acetate, pH 7.4 (25 mM TRIS), spermine (1 mM) and ethyleneglycol (20 vol-%) and incubated for 10 minutes at 0° C. Cleavage reactions were initiated by addition of 2 mM DTT, proceeded 16 hours at 0° C. to 25° C., and stopped by precipitation with ethanol. The reaction products were analyzed on a high resolution polyacrylamide gel. For each lane the parameters differing from these general conditions are given below. (lane 21): Control, minus oligonucleotide DNA-EDTA; (lanes 22, 27 and 32): 1 μM oligonucleotide DNA-EDTA 6; (lanes 23, 28 and 33): 1 μM oligonucleotide DNA-EDTA 5; (lanes 24, 29 and 34): 1 μM oligonucleotide DNA-EDTA 4; (lanes 25, 30 and 35): 1 μM oligonucleotide DNA-EDTA 7 (Hoogsteen-type TG-mismatch); (lanes 26, 31 and 36): 1 μM oligonucleotide DNA-EDTA 8 (Hoogsteen-type CA-mismatch). The reactions were run for 16 hours at 0° C. (lanes 22 to 26), 12.5° C. (lanes 27 to 31) and 25° C. (lanes 21 and 32 to 36) respectively. Electrophoresis on a 5 percent polyacrylamide gel separated the radiolabeled 628 bp fragment from other digest products.

FIG. 4B shows the sequence of oligonucleotide DNA-EDTA probes 4–9 where T* is the position of the thymidine-EDTA. Histograms shown in this figure of the DNA-cleavage patterns were determined by densitometry of the autoradiogram from the cleavage of the 628 bp restriction fragment with oligonucleotide DNA-EDTA probes 4 and 9.

On the 3' end-labeled DNA-strand, carrying the pyrimidine-rich sequence, DNA-EDTA-Fe(II) 4 and 9 both produce sequence specific cleavage patterns shifted to the 5' side of the T* position (FIG. 4B) consistent with major groove binding. The efficiency of the sequence specific cleavage of the DNA restriction fragment by oligonucleotide DNA-EDTA-Fe(II) 4 is dependent on spermine and/or Co(NH$_3$)$_6$$^{+3}$-concentrations, ethylene glycol, pH and probe concentration (FIG. 5A).

The cleavage efficiency of oligonucleotide probes 4–6 which differ in length (15, 13 and 11 nucleotides) and oligonucleotide probes 7 and 8 which differ in sequence (each contain one Hoogsteen base mismatch in the triple helix complex) were examined under identical conditions at different temperatures. Identical cleavage patterns are observed for the oligonucleotide DNA-EDTA-Fe(II) probes 4–8. At 0° C., oligonucleotide probes 4–6 which differ in length but have in common T* at position 5 each produce a cleavage pattern of the same intensity. At 25° C. oligonucleotide probe 6 which is 11 nucleotides in length cleaves the target DNA 3 times less efficiently than oligonucleotide probes 5 or 4 which are 13 and 15 nucleotides in length, respectively. Oligonucleotide DNA-EDTA probes 7 and 8 which contain a single base mismatch at position 10 and 11 generate cleavage patterns of reduced intensity and is temperature sensitive. Compared to oligonucleotide DNA-EDTA probe 4, the relative cleavage efficiency decreases for the single base mismatch probes 7 from 0.4 (at 0° C.) to 0.08 (25° C.) and 8 from 0.5 (at 0° C.) to 0.13 (25° C.) (FIG. 5B).

Optimization of Assay Conditions

In this example, the effect of added cations, organic solvents, pH, temperature, oligonucleotide probe length and sequence homology were studied. The results, detailed below, are summarized in FIG. 5.

FIG. 5A shows a bar graph presenting the absolute cleavage efficiencies obtained with oligonucleotide DNA-EDTA-Fe probe 4 under various conditions. The values were determined by cutting out the corresponding pieces of the dried gel and measuring their radioactivity by scintillation counting. The numbers given are calculated by dividing the radioactivity of the cleavage site (sum of 5 most efficiently cleaved nucleotides) with the total radioactivity obtained from the uncleaved fragment, the cleavage site and the background, which is corrected for the background that resulted from the untreated 628 bp fragment. The remaining values were assigned by correlation of absolute with relative cleavage efficiencies determined by densitometry of the autoradiogram. FIG. 5(B) shows a bar graph presenting the relative cleavage efficiencies (sum of 6 most efficiently cleaved nucleotides) obtained with oligonucleotide DNA-EDTA-Fe probes 4–8 (FIG. 4A) at three temperatures as determined by densitometry. The data is reproducible within +10% of reported values.

Importance of Added Cations

The importance of added cations for formation of triple-stranded DNA or RNA has been known since the discovery of those structures. To bind double-helical DNA, the oligonucleotide DNA-EDTA-Fe(II) probe must overcome the repulsion between two anionic chains of the Watson-Crick duplex and its own negatively charged phosphodiester backbone. One way to achieve this is to use multivalent cations (Michelson, et al., *Nucl. Acid. Res. Mol. Biol.* 6:83 (1967); and Felsenfeld and Miles, supra). The naturally occurring polyamines and their derivatives are known to stabilize double- and triple helical structures of nucleic acids. (Blaser and Gabbay, *Biopolymers* 6:243 (1968)). We find preferred cleaving efficiencies for oligonucleotide DNA-EDTA-Fe(II) probe 4 in the presence of mM concentrations of spermine or $Co(NH_3)_6^{+3}$. No cleavage occurs in the absence of spermine or $Co(NH_3)_6^{3+}$ which demonstrates the importance of these or similar cations for triple helix formation (FIG. 5A). Spermine appears to be ideal for the stabilization of the triple-stranded complex with oligonucleotide DNA-EDTA-Fe(II) probes. It efficiently neutralizes the negative charges of the sugar-phosphate backbones and does not compete with the Fe(II) for the EDTA-moiety. No cleavage is observed if $MgCl_2$ or $CaCl_2$ (up to 8 mM) are substituted for spermine which could also be due to competition with Fe(II) for the metal chelator EDTA (Hertzberg and Dervan, *Biochemistry* 23:3934 (1984)).

Role of Organic Solvents

According to x-ray fiber diffraction studies, the three strands of a triple helix occur in a A'RNA-like conformation (Arnott, *Nucl. Acids Res.* 3:2459 (1976)). A conformational transition may be necessary to allow the binding of the oligonucleotide DNA-EDTA-Fe(II) probe. It is established that a B to A conformational change takes place on lowering the relative humidity. This transformation is dependent on the ratio of (A+T) to (G+C) and can be achieved by the addition of a variety of organic solvents to the DNA aqueous solution. The increase in organic solvent concentration should favor the B to A conformational transition and suggest that triple helices should form more readily (Saenger, *Principles of Nucleic Acid Structure*, edited by C. R. Cantor, Springer-Verlag, New York, Inc. (1984)). As a result, the cleavage due to the oligonucleotide DNA-EDTA probe should increase correspondingly. We find that the efficiency of duplex cleavage by oligonucleotide $(T)_{15}$-EDTA-Fe(II) probes 1–3 is increased by a factor of 10 upon addition of ethyleneglycol (40 percent by volume). Other organic solvents such as methanol, ethanol, dioxane or DMF give rise to similar behavior. In the presence of ethyleneglycol, oligonucleotide DNA-EDTA-Fe(II) probes provide cleavage patterns without detectable background, a result that may be due to radical scavenging by this solvent.

Curiously, the mixed T and C pyrimidine-rich oligonucleotide EDTA-Fe(II) probe 4 demonstrates different behavior. The addition of 20 vol-% ethyleneglycol is not necessary and does not increase the cleavage efficiency as found in the $(T)_{15}$ case. One explanation for this difference is that a mixed T, C oligonucleotide probe may have a higher affinity than the oligo T probe to the corresponding Watson-Crick target sequence due to the protonated cytosines required to form the Hoogsteen-hydrogen bonds in the triple helix. The alternative explanation is that the target Watson-Crick sequences differ in conformation and one may be more A like than the other.

The pH-Dependence of Cleavage Efficiency

Mixed pyrimidine-rich oligonucleotide DNA-EDTA-Fe (II) probe 4 cleaves double-helical DNA over a relatively narrow range of pH values producing the maximum cleavage at pH 7.0 (FIG. 5A) (the pH values are not corrected for temperature or different ethyleneglycol percentage and are given for the tenfold concentrated buffer solutions at 25° C.). This behavior could be caused by two independent properties of the oligonucleotide-EDTA probes. On one hand, triplex formation requires protonation of cytosines at N-3 in the third strand to enable the Hoogsteen hydrogen bonds between oligonucleotide DNA-EDTA-Fe(II) probes and the target Watson-Crick DNA sequence. It was previously demonstrated that complexes of triple helical nucleic acids, containing cytosines in the homopyrimidine strands, are stable in slightly acidic to neutral solutions and start to dissociate on increasing pH (Lipsett, *J. Biol. Chem.* 239:1256 (1964); Morgan and Wells, *J. Mol. Biol.* 37:63 (1969)). Therefore it seems not unreasonable that the oligonucleotide DNA-EDTA-Fe(II) probes do not bind Watson-Crick DNA in slightly basic solutions (pH≧8) and consequently do not produce cleavage under these conditions. On the other hand, studies with methidiumpropyl-EDTA-Fe indicate that the cleavage efficiency of EDTA-Fe decreases sharply below pH 7 (Hertzberg and Dervan, supra), presumably due to either partial protonation of the EDTA and the resulting loss of Fe(II) or some pH-dependence of the cleavage reaction. Based on known EDTA cleavage chemistry, it is anticipated that at slightly acidic pH-values, oligonucleotide DNA-EDTA-Fe(II) probes do not produce efficient cleavage. In data not shown, footprinting experiments confirm that the triple helix is forming at acidic pH values.

Influence of Probe Length, Temperature, and Sequence Homology

At 1 uM concentration the oligonucleotide DNA-EDTA probe approaches the maximum cleavage efficiency on the 628 bp restriction fragment (FIG. 5A). We chose oligonucleotide DNA-EDTA probes 13 nucleotides in length for our initial studies to attain reasonable binding affinities at the double-helical target sequence (Cassani and Bollum, *Biochemistry* 8:3928 (1969); Raae and Kleppe, *Biochemistry* 17:2939 (1978)). Having determined the preferred cleavage conditions for oligonucleotide DNA-EDTA-Fe(II) probe 4, we focused on the size dependence for oligonucleotide DNA-EDTA-Fe(II) probes to form a triple helix complex with the Watson-Crick DNA. Oligonucleotide DNA-EDTA-Fe(II) probes 5 and 6, which are 13 and 11 nucleotides in size, produce cleavage patterns of similar intensities at 0° C., indicating that homopurine-homopyrimidine sequences as short as 11 nucleotides can specifically bind the 628 bp restriction fragment. The influence of oligonucleotide length becomes more apparent if the cleavage reactions are allowed to proceed at higher temperatures. Oligonucleotide DNA-EDTA probes 4 and 5 cleave the target duplex DNA at 25° C. with approximately the same efficiency, whereas the relative intensity of the cleavage pattern produced by the shorter oligonucleotide probe 6 becomes significantly weaker (FIGS. 4A, 5B).

In order to test the importance of sequence homology for triple helix formation and cleavage, two probes, oligonucleotide DNA-EDTA-Fe(II) probes 7 and 8, were synthesized that contained single base mismatches compared to oligonucleotide DNA-EDTAFe(II) 4 probe but had in common the location of T* at position 5. When bound to the double-helical target sequence, probes 7 and 8 should give rise to one mismatched base-triplet with respect to the Hoogsteen hydrogen bonding. The mismatching bases in the oligonucleotide probe strands were chosen so that the corresponding tautomeric or protonated structures of the mismatching pyrimidine base could still allow the formation of isomorphous base triplets. Compared to oligonucleotide DNA-EDTA-Fe(II) probe 4, both single mismatch probes 7 and 8 generate weaker cleavage patterns at 0° C. and the difference becomes more apparent for the cleavage patterns produced at 25° C. (FIG. 5B). Oligonucleotide probes 7 and 8 cleave the target DNA less efficiently than the corresponding homologous oligonucleotide DNA-EDTA-Fe(II) probe 4. This result indicates that a single base-mismatch in an oligonucleotide DNA-EDTA-Fe(II) probe, 15 nucleotides in length, can lower the cleavage efficiency by at least a factor of 10. Clearly, the sequence specific recognition of large double-helical DNA by oligonucleotide DNA-EDTA-Fe(II) probes is sensitive to single base mismatches indicating the importance of the correct pyrimidine-rich probe sequence for the formation of a triple-stranded complex with the target-DNA.

EXAMPLE 3

Site Specific Double-Strand Cleavage of Plasmid DNA

The ability of oligonucleotide DNA-EDTA-Fe(II) probe 9 to cause double-strand breaks at a homopurine-homopyrimidine insert in large DNA is presented in FIG. 6A. This figure shows double-strand cleavage of plasmid DNA analyzed on a nondenaturing 0.9% agarose gel. The plasmid pDMAG10 (Mendel and Dervan, *Proc. Natl. Acad. Sci. USA* 84:910 (1987)) was digested with StyI restriction endonuclease to produce a linear DNA fragment 4.06 kb in size which contains the homopurine site $d(A_5(AG)_5)$ located 1.0 kb upstream from the restriction site. This affords heterogenous overhangs and each end could be labeled separately using either $\alpha$-$^{32}$P-ATP or $\alpha$-$^{32}$P-TTP according to standard procedures. Lanes 1–3 of FIG. 6A shows plasmid pDMAG10 linearized with StyI and labeled at the downstream end of the restriction site with $\alpha$-$^{32}$P-ATP. Lanes 4–6 show the same plasmid with the other end labeled with $\alpha$-$^{32}$P-TTP.

The $^{32}$P-end-labeled DNA was allowed to incubate with oligonucleotide DNA-EDTA-Fe(II) probe 9 (5 $\mu$M) for 10 minutes at 0° C. as previously described and the cleavage reaction was initiated by the addition of DTT (2 mM) and run at 0° C. for 16 hours. Cleavage conditions included $^{32}$P labeled DNA plasmid, 100 mM NaCl, 1 mM spermine, 25 mM TRIS/acetate pH 7.0, 100 $\mu$M (bp) sonicated, deproteinized calf thymus DNA, 5 yM oligonucleotide DNA-EDTA-Fe(II) probe 9, 25 $\mu$M Fe(II) and 2 mM DTT. Lanes 1 and 4 are controls containing no oligonucleotide DNA-EDTA-Fe(II) probe 9. Lanes 2 and 5 are DNA size markers obtained by digestion of StyI linearized pDMAG10 with EcoRI, PvuI, SalI (both ends labeled), and Xmn I labeled with $\alpha$-$^{32}$P-TTP): 4058 (undigested DNA), 53338, 2994, 2368, 1690, 1460, 1064, and 720. Lanes 3 and 6 are oligonucleotide DNA-EDTA-Fe(II) probe 9 at 5 $\mu$M added.

Separation of the cleavage products by agarose gel electrophoresis followed by autoradiography reveals only one major cleavage site producing two DNA fragments, 3.04 and 1.02 kb in size as determined by comparison with comigrating DNA size markers (FIG. 6A, lanes 3 and 6).

FIG. 6B (left) shows the course resolution cleavage pattern from gel 6A. FIG. 6B (middle) depicts a simplified model of the triple helix complex with the Hoogsteen bound oligonucleotide DNA-EDTA-Fe(II) probe 9 at one unique site within 4.06 kb of plasmid DNA. The high resolution cleavage pattern at that site is shown in FIG. 4B.

This example demonstrates that pyrimidine-rich probes can recognize a purine-rich target sequence in a very large piece of double-stranded DNA to form a triple helix under physiological conditions.

EXAMPLE 4

The Orientation of a Purine-Rich Oligonucleotide Bound in the Major Groove of Double-Helical DNA is Antiparallel to the Purine-Rich Strand The target binding site chosen was a 19-bp purine-rich sequence, 5'-$AG_3AG_4AG_4$-$AG_3$A-3', within a 648-bp restriction fragment. The target sequence is identically read from 3' to 5' or 5' to 3'. Therefore, it could a priori support two putative triple helical structures within a purine-purine-pyrimidine motif with the third strand parallel or antiparallel to the W-C purine strand. Oligonucleotides 1 to 3 of sequence composition 5'-T*$G_3XG_4XG4XG_3$T-3' (where X=T,A,C, respectively) were synthesized with thymidine-EDTA (T*) at each 5' end.

FIG. 8A contains an autoradiogram of an 8% polyacrylamide sequencing gel showing the dependence of cleavage efficiency on sequence composition of oligonucleotides 1 to 3, each at three different concentrations (0.1, 0.5, and 1.0

μM). The cleavage reactions were performed on the Hind III-Ssp I restriction fragment of plasmid pPBAG19 labeled at the 3' end with $^{32}$P. The plasmid pPBAG19 was constructed by inserting the sequence d($A_2T_2(CT)_3$ $A_5G_3AG_4AG_4AG_3A_5$-$(CT)_3$) into the large Eco RI-Xba I restriction fragment of pUC19. Reactions were performed on the 3' end-labeled Hind III-Ssp I restriction fragment. The reactions were carried out by combining a mixture of oligonucleotide-EDTA and 2.5 equivalents of Fe($NH_4$)$_2$ ($SO_4$)$_2$.6$H_2O$ with the $^{32}$P-labeled restriction fragment [~100 nM in base pairs, ~10,000 cpm] in a solution of tris acetate, pH=7.8 (50 mM), NaCl (10 mM), spermine (100 μM), and calf thymus DNA (100 μM in base pairs), which was then incubated at 24° C. for 1 hour. Cleavage reactions were initiated by the addition of dithiothreitol (DTT) (4 mM) and allowed to proceed for 12 hours at 24° C. The reactions were stopped by precipitation with ethanol, and the cleavage products were analyzed by gel electrophoresis. Lane 1 contains products of an A-specific cleavage reaction (The plasmid pPBAG19 was constructed by inserting the sequence d($A_2T_2(CT)_3A_5G_3AG_4AG_4AG_3A_5$-$(CT)_3$) into the large EcoRI-XbaI restriction fragment of pUC19. Reactions were performed on the 3' end-labeled Hind III-Ssp I restriction fragment.) Lane 2 is a control showing the intact 3' end-labeled restriction fragment obtained after treatment according to the cleavage reactions in the absence of oligonucleotide-EDTA.Fe. Lanes 3 to 11 show the cleavage products produced by oligonucleotides-EDTA-Fe of general sequence T*$G_3XG_4XG_4XG_3$T-3'. In lanes 3 to 5, X=T, in lanes 6 to 8, X=A, and in lanes 9 to 11, X=C. The concentration of the oligonucleotide-EDTA-Fe probes 1 to 3, in lanes 3, 6 and 9 was 1 to 3 at 0.1 μM. In lanes 4, 7 and 10, the oligonucleotide probe concentration was 0.5 μM. Finally, the oligonucleotide probe concentrations in lanes 5, 8 and 11 was 1.0 μM. Cleavage efficiencies were quantitated by using storage phosphorimaging plates with a Molecular Dynamics 400S PhosphoImager.

The oligonucleotide EDTA-Fe probes cleaved the double-helical DNA at the target site but with different efficiencies. Cleavage occurred near the 3' end of the purine-rich target sequence. The cleavage maximum on each strand was shifted asymmetrically in the 5' direction. The asymmetry and location of the cleavage pattern on one end of the binding site indicate that oligonucleotides 1 to 3 were bound in the major groove anti-parallel to the W-C purine strand. This result rules out strand displacement (D-looping) as the mode of recognition. No cleavage products corresponding to a parallel orientation could be detected. A ribbon model and sequence of the local triple helical complex between oligonucleotides-EDTA-Fe 1 to 3 and the target sequence is set forth in FIG. 7B. The circles represent backbone positions of cleavage. The size of circles represent extent of cleavage. The third strand is located near the center of the major groove of the double-helical DNA based upon the models of triplet formation in FIG. 9A. In FIG. 9A the models for G.GC, A.AT, and T.AT triplets within a triple helix motif are shown were the third strand is anti-parallel to the purine W-C strand and bases are in the anti-conformation. FIG. 9B on the other hand shows models for G.GC, A.AT, and T.AT triplets where the third strand is anti-parallel to the purine W-C strand and the bases are in the syn conformation. In both FIGS. 9A and 9B, plus and minus indicate relative polarities of the phosphate-deoxyribose backbones.

From phosphorimager quantitative analysis of the absolute cleavage efficiencies, oligonucleotides 1 to 3 at 1.0 μM concentration appeared to bind the target sequence with relative affinities 1.0 (X=T), 0.56 (X=A), and 0.16 (X=C), respectively. Therefore, for this particular sequence and under these reaction conditions, the contribution to the stability of the triple helix from three A.AT triplets differed from that of three T.AT triplets by less than a factor of 2. However, when C was placed opposite three AT base pairs, the binding of the oligonucleotide decreased by nearly a factor of 8. Although the binding of oligonucleotides 1 to 3 is dominated by the formation of G.GC triplets, we believe the difference in affinities for 1 to 3 may be evidence for specific hydrogen bond contributions in the T.AT and A.AT triplets (FIG. 9).

The efficiency of strand scission depended upon the concentration of multivalent cations such as spermine and $Mg^{2+}$, with maximum cleavage occurring $\geq$100 μM concentration of spermine. Cleavage efficiencies were comparable throughout the pH range 6.6 to 7.8. The pH dependence on the recognition of G-rich sequences through pyrimidine oligonucleotide-directed triple helix formation is well documented (Moser and Dervan, Science 238:645 (1987); Strobel, S. A., Moser, H. E., Dervan, P. B., J. Am. Chem. Soc. 110:7927 (1988); Povsic, T. J. and Dervan, P. B., ibid., 111:3059 (1989); Strobel, S. A. and Dervan, P. B., ibid. p. 7286; Luebke, K. J. and Dervan, P. B., ibid., p. 8733; Horne, D. A. and Dervan, P. B., ibid., 112:2435 (1990); Strobel, S. A. and Dervan, P. B., Science 249:73 (1990); Maher, L. J. III, Wold, B., Dervan, P. B., Science 245:725 (1989); Griffin, L. C. and Dervan, P. B., ibid., p. 967; Praseuth, D., et al., Proc. Natl. Acad. Sci. USA 85:1349 (1988); Francois, J. C., Saison-Behmoaras, T. C., Chasignol, M., Thuong, N. T., Helene, C., J. Biol. Chem. 264:5891 (1989); Lyamichev, V. I., Mirkin, S. M., Frank-Kamenetskii, M. D., Cantor, C. R., Nucl. Acids Res., 16:2165 (1988); Francois, J. C., Saison-Behmoaras, T., Thuong, N. T., Helen, C., Biochemistry 28:9617 (1989); Sun, J. S., et al., Proc. Natl. Acad. Sci. USA 86:9198 (1989); Rajogopal, P. and Feigon, J., Nature 339:637 (1989)). The apparent requirement for protonation of cytosines in the third strand to form C+GC triplets limits the pH range (typically $\leq$pH 7.0) within which this triple helical structure can be formed. With oligonucleotide-EDTA probes 1 and 2, for which the target duplex is 75% guanine-rich, we observed efficient cleavage at pH 7.8. Therefore, purine-rich oligonucleotides bound double-helical DNA in a relatively pH-independent fashion.

Within the constraints of our experimental data that the third strand is anti-parallel to the purine-rich W-C strand, models of possible hydrogen-bonding patterns for A.AT, T.AT, and G.GC base triplets place the phosphate-deoxyribose backbone in different locations in the major groove depending on whether the base in the third strand is in the anti- or syn-conformation (FIG. 9). The anti-conformation would generate a structure with the phosphate-deoxyribose backbone centrally located in the major groove of the double-helix (FIG. 8A). The syn-conformation would place the backbone in a similar location in the major groove as found with the pyrimidine motif (FIG. 9B).

Although reasonable hydrogen-bonding models for T.AT and G.GC triplets can be written for both the syn- or anti-conformations of the third strand, models for the A.AT triplet suggest the most reasonable structure is the anti-conformation (FIG. 9A). Hence, we tentatively favor the anti-conformation and placement of the phosphate-deoxyribose backbone near the center of the major groove located more equidistant between the W-C strands (FIG. 9A). This triple helix structure differs from the pyrimidine-rich motif in which the phosphate-deoxyribose backbone is located proximal (and parallel) to the purine-rich W-C strand.

EXAMPLE 5

This example describes the design of heterocycles for the recognition of CG Watson-Crick base pairs within the pur..pur.pyr triple helical motif. Model building studies suggested that the deoxyribonucleoside 2'-deoxynebularine (N) would fulfill this role (FIG. 10). It was assumed that the purine core of 2'-deoxynebularine would mediate base stacking interactions in the third strand. In addition, the heterocyclic ring system provides a hydrogen bond acceptor (N1) which should allow the formation of one hydrogen bond to the exocyclic amino group of cytosine or adenine (FIG. 10).

The affinity cleaving method was used to analyze the binding of 2'-deoxynebularine (N) to all four possible combinations of the two Watson-Crick base pairs. It was found that within the particular DNA sequence studied N interacts preferential with CG base pairs. The new recognition element was employed to target a single site of the HIV genome containing two CG base pairs within plasmid DNA.

Deoxynebularine phosphoramidite was purchased from Glen Research. All other phosphoramidites and chemicals for DNA synthesis were obtained from Applied Biosystems Inc. Restriction endonucleases and all other enzymes were purchased from Boehringer-Mannheim, New England Biolabs or Sigma. The Sequenase™ DNA sequencing kit (Version 2.0) was obtained from United States Biochemical Inc. Deoxynucleoside triphosphates (100 mM solutions), calf thymus DNA and Nick™-columns were purchased from Pharmacia LKB. The radiolabeled triphosphates 5'-($\alpha$-$^{32}$P) dGTP (>3000 Ci/mmol), 5'($\gamma^{32}$p) ATP(>5000 Ci/mmol) and 5'-($\alpha$-$^{35}$S)dATP (>1000 Ci/mmol) were obtained from Amersham. All other chemicals were of analytical or HPLC grade.

Whenever possible, standard molecular biological methods were used (Sambrook, J., Fritsch, E. F., Maniatis, T. (1989) in Molecular Cloning: A Laboratory Manual, 2nd ed., Cold Spring Harbor Laboratory Press, Cold Spring Harbor, N.Y.). Agarose gel electrophoresis was performed in 1×TAE buffer and polyacrylamide gel electrophoresis was carried out in 1×TBE buffer (Sambrook et al., ibid.). Cerenkov radioactivity was measured with a Beckman LS 2801 scintillation counter.

Oligodeoxynucleotides were synthesized on an Applied Biosystems Model 3808 DNA synthesizer using $\beta$-cyanoethyl phosphoramidite triester chemistry (Beaucage, S. L., and Caruthers, M. 1-1. (1981) Tetrahedron Lett. 22, 1859–1862; Sinha, N. D., Biernat, J., McManus, J., Koster, H. (1984) Nucleic Acids Res. 12:4539–4557) The nucleoside analog T* was prepared according to published procedures and was incorporated at the 3' end of oligodeoxynucleotides via the 5'-O-DMT-thymidine-EDTA-triethylester-3'-succinyl controlled pore glass (Dreyer, G. B., and Dervan, P. B. (1985) Proc. Natl. Acad Sci. USA 82:968–972). Unmodified oligodeoxynucleotides were deprotected under standard conditions using concentrated ammonium hydroxide. Oligodeoxynucleotides containing the nucleoside analog T* were treated with 0.1N NaOH (1.5 mL) at 55° C. for 24 hours. The DMT protected oligomers were purified by reverse phase FPLC chromatography (Pharmacia ProRPC 15 mm HR 10/10; gradient of 0–40% acetonitrile in 100 mM triethylammonium acetate (pH=7.0)). Lyophilized fractions were treated (20 min, 23° C.) with an 80% solution of acetic acid in water (500 $\mu$l) in order to remove the DMT protecting group. The oligomers were then repurified by FPLC. The concentrations of the oligodeoxynucleotides were determined by UV measurements ($A_{260}$), using the following molar extinction coefficients: 15400 (A), 11700 (G), 7300 (C), 8800 (T and T*), and 6000 (N) $cm^{-1}M^{-1}$. After lyophilization the oligodeoxynucleotides were stored dry at −78° C.

Analytical HPLC was performed with a Hewlett-Packard 1090 Liquid Chromatograph using a reverse phase VYDAC 1090 201HS54 4.6 mm×25 cm 5 micron C18 column. The purified oligodeoxynucleotides (3 nmol) were digested simultaneously with snake venom phosphodiesterase (3 $\mu$L, 2.4 $\mu$g/$\mu$L) and calf intestine alkaline phosphatase (3 $\mu$L, 1 U/$\mu$L) in 50 mM Tris-HCl (pH 8.1), 100 mM $MgCl_2$. The reaction mixture was incubated at 37° C. for 3 h, filtered through a 0.45 $\mu$m Nylon-66 syringe filter (Rainin) and lyophilized. The sample was dissolved with 10 $\mu$L of 10 mM ammonium phosphate (pH=5.1)/8% methanol buffer, and an aliquot of the solution was injected onto the C18 reverse phase column. The products were eluted with 10 mM ammonium phosphate (pH=5.1)/8% methanol and detected at $A_{260}$. Comparison with standard solutions of A, T and N established the composition of the oligodeoxynucleotides.

Affinity Cleaving Reactions of 39mer Duplex Targets

For the preparation of the duplex targets, each single-stranded oligodeoxynucleotide (100 pM) of sequence composition 5'd($A_2T_2(CT)_3A_5G_3XG_4AG_4AG_3A_5(CT)_3$)3' (X=A, G, C, or T) was 5' end labeled using T4 polynucleotide kinase and $\gamma$-$^{32}$P ATP according to standard procedures (Sambrook et al., supra.). The reaction mixture was twice extracted with TE buffer-saturated phenol (1.0 volume) and twice extracted with 24:1 chloroform/isoamyl alcohol (1.0 volume). The DNA was ethanol precipitated, and the radiolabeled oligodeoxynucleotides were annealed to their unlabeled complementary oligodeoxynucleotides. The resulting duplexes were purified on 15% nondenaturing polyacrylamide gels (19:1; monomer/bis). Gel bands were visualized by autoradiography and desired bands were excised from the gel, crushed and eluted with 1 mL 200 mM NaCl at 37° C. for 20 h. The eluents were passed through 0.45 $\mu$m Centrex filters and lyophilized. The residue was taken up in 100 $\mu$L distilled water and the solution was then desalted by passing it through a Nick™-column. The radiolabeled duplex-DNA was finally isolated by ethanol precipitation.

Specific DNA cleavage reactions for adenine were performed as described previously (Iverson, B. L., and Dervan, P. B. (1987) Nucleic Acids Res. 15:7823–7830). The affinity cleaving reactions were executed in a total volume of 80 $\mu$L by combining a mixture of oligodeoxynucleotide-EDTA (100 nM) and $Fe(NH_4)_2(SO_4)_2 \cdot 6H_2O$ (250 nM) with the $^{32}$P-labeled duplex (~120 000 cpm) in a solution of tris-acetate (50 mM, pH=7.4 at 23° C.), NaCl (20 mM), spermine (100 $\mu$M) and calf thymus DNA (100 $\mu$M in base pairs). The oligodeoxynucleotide probe was allowed to equilibrate with the DNA duplex target at 37° C. for 4 hr. The cleavage reactions were then initiated by the addition of dithiothreitol (4 mM final concentration) and allowed to proceed at 37° C. for 14 h. The reactions were quenched by freezing (liquid $N_2$) followed by lyophilization. The residue was suspended in 10 $\mu$L formamide loading buffer (90% formamide, 10% 10×TBE buffer, 0.02% bromophenol blue, 0.02% xylene cyanol) and transferred to new tubes. The DNA suspensions were assayed for specific activity by scintillation counting and diluted to 5000 cpm/$\mu$L. The cleavage products were denatured at 90° C. for 5 min and 4 $\mu$L of each sample were separated by 20% denaturing polyacrylamide gel electrophoresis (19:1; monomer/bis). The gels were exposed to X-ray film (Amersham Hyperfilm™-MP) at −78° C. with a single intensification screen or to a storage phosphor screen.

Quantitation of Cleavage Efficiencies by Storage Phosphor Technology Autoradiography The relative cleavage efficiencies were determined by quantitation on a Molecular Dynamics 400S Phosphorimager. Gels were exposed to the storage phosphor screen (Kodak storage screen S0230 obtained from Molecular Dynamics) in the dark at 23° C. for 4 h (Johnston, R. F., Pickett, S. C., and Barker, D. L. (1990) *Electrophoresis* 11:355–360). The data were analyzed using the ImageQuant v. 3.0 software. The radiation background of the screen was determined by performing volume integrations over four independent reference sites. All other volume integrations were based on the averaged background value obtained. Integration of the cleavage bands was performed over the five most efficiently cleaved nucleotides. Rectangles of the same size were used for each lane and the amount of radioactivity found in the respective untreated control lane was subtracted from the obtained values. The relative cleavage efficiencies were evaluated by calculating the ratio of the radioactivity of the site-specific cleavage band by the integrated volume of the entire lane. The given values represent the average over two independent experiments.

Construction of the Plasmid pULHIV

The plasmid pULHIV was obtained by cloning the oligodeoxynucleotides 5'd($A_2T_2CG_2C$-$A_2GAG_2$-$CGAG_4CG_2CGACT$)3' and 5'd(CTAGAGT-$CGC_2GC_4TCGC_2TCT_2GC_2G$)3' into the large EcoRI/XbaI restriction fragment of pUC19 by using T4 DNA Ligase. The ligation mixture was employed to transform Epicurian™ Coli XL1 Blue competent cells (Stratagene). The cells were grown on Luria Bertani medium agar plates containing 100 μg/mL ampicillin, X-gal, and IPTG. Large scale plasmid isolation of appropriate clones was performed using QIAGEN purification kits (Diagen) according to the manufacturer's protocol. The sequence of the insert was subsequently confirmed by dideoxynucleotide sequencing (Sanger, F., Nicklen, S., and Coulson, A. R. (1977) *Proc. Natl. Acad. Sci. USA* 72:2251–2255) using the #1201 M13 reverse sequencing primer (New England Biolabs).

Affinity Cleaving Reactions of the pULHIV EcoO1091-SspI Restriction Fragment The pULHIV EcoO1091-SspI restriction fragment was produced as follows. Plasmid DNA (20 μg) was linearized with EcoO1091 and then end labeled with 5'-(α-$^{32}$P)dGTP employing sequenase™ (version 2.0) as the enzyme. The reaction mixture was applied to a Nick™-column to remove unincorporated radiolabeled nucleotide triphosphates. The labeled DNA was then ethanol precipitated and digested with SspI. The resulting 3'-$^{32}$P-end labeled fragment (2515 bp) was purified by agarose gel electrophoresis (1% Nusieve GTG Agarose, FMC). Gel bands were visualized by autoradiography, the desired band was excised from the gel and transferred to an eppendorf tube. The agarose was frozen and thawed (3×) and the resulting suspension was centrifuged (20 min, 14K). The supernatant was removed and was twice extracted with TE buffer saturated phenol (1.0 volume) and twice extracted with 24:1 chloroform/isoamyl alcohol (1.0 volume). The DNA was ethanol precipitated, dissolved in 100 μL TE buffer and then passed through a Nick™-column. Finally the DNA was ethanol precipitated and dissolved in water to a final concentration of 10000 cpm/μL.

The affinity cleaving reactions were executed in a total volume of 80 μL by combining a mixture of oligodeoxynucleotide-EDTA (2 μM) and Fe($NH_4$)$_2$($SO_4$)$_2$·6$H_2$O(5 μM) with the $^{32}$P-labeled restriction fragment (~40 000 cpm) in a solution of tris-acetate (50 mM, pH 7.4 at 23° C.), NaCl (10 mM), spermine (1 mM) and calf thymus DNA (100 μM in base pairs). The oligodeoxynucleotide probe was allowed to equilibrate with the DNA duplex target at 37° C. for 4 h. The cleavage reactions were then initiated by the addition of dithiothreitol (4 mM) and allowed to proceed at 37° C. for 12 h. The reactions were stopped by precipitation of the DNA with ethanol. The residue was resuspended in TE buffer (30 μL) and transferred to new tubes. The DNA suspensions were assayed for specific activity by scintillation counting and diluted to 5000 cpm/20 μL. An aliquot (10 μL) of glycerol gel loading buffer (30% glycerol in water, 0.25% bromophenol blue, 0.25% xylene cyanol) was added to 20 μL of each of the samples. The cleavage products were separated by 5% nondenaturing polyacrylamide gel electrophoresis (19:1 monomer/bis). The gel was dried on a slab dryer and visualized by autoradiography (Amersham Hyperfilm™-MP, −78° C., intensification screen).

Synthesis of Oligodeoxynucleotides Containing 2'-Deoxynebularine and Base Composition Analysis Oligodeoxynucleotides 1–17 were synthesized by solid phase methods using β-cyanoethyl phosphoramidite chemistry (Beaucage, S. L., amd Caruthers, M. 1-1. (1981) *Tetrahedron Lett.* 22:1859–1862; Sinha, N. D., Biernat, J., McManus, J., Koster, H. (1984) *Nucleic Acids Res.* 12:4539–4557). The 2'-deoxynebularine phosphoramidite coupled as efficiently as the A, G, C, and T phosphoramidites. The base composition of oligodeoxynucleotides 1, 6, 11, 16, and 17 containing 2'-deoxynebularine were established by HPLC analysis. For this, the oligodeoxynucleotides were treated with snake venom phosphodiesterase and calf intestine phosphatase. The nucleoside monomers obtained were separated by HPLC and identified by their HPLC retention times and UV spectra. Comparison of the integrated areas of the HPLC peaks with that of standard solutions of A, T and N confirmed the correct base composition of the oligodeoxynucleotides.

Analysis of Binding Specificity

The relative affinity of 2'-deoxynebularine for all four Watson-Crick base pairs within a pur.pur.pyr triple-helix motif was examined by affinity cleaving (Dreyer and Dervan, 1985, supra.). A series of 15 nt oligodeoxynucleotides 1–5 (FIG. 11), differing at one base position 5'd ($TG_4TG_4ZG_3T*$)3' (Z=N, A, G, C, or T); and equipped with the DNA cleaving moiety, thymidine-EDTA-Fe(II) (T*) at a single thymidine position at the 3' end was prepared. The relative stabilities of the triple helical structures formed upon complexation of these oligodeoxynucleotides with 39-bp DNA duplexes containing one variable base pair site 5'-$^{32}$P-$A_2T_2$(CT)$_3A_5G_3XG_4AG_4AG_3A_5$(CT)$_3$)3' . 5'-d(CT (AG)$_4T_5C_3TC_4TC_4YC_3T_5$(AG)$_3$)3' (XY=AT, CG, GC, or TA) were then measured. The DNA affinity cleaving reactions were performed under conditions which allowed the difference in stability between single base triplets to be distinguished (100 nM oligodeoxynucleotide-EDTA, 100 μM spermine, 20 mM NaCl). The most efficient cleavage was observed for the combinations Z=A or T, XY=AT, and Z=G, XY=GC (results not shown). These cleavage patterns reflect the known ability of G, A, and T to form G.GC, A.AT, and T.AT base triplets, respectively (Beal, P. A., and Dervan, P. B. (1991) *Science* 251:1360–1363).

Importantly, intense cleavage was also detected for a N.CG triplet (results not shown). The base triplets N.AT, C.AT, T.CG, and A.GC produced moderate cleavage. Only weak cleavage was observed for the 12 additional triplet combinations. The relative cleavage intensities were determined by quantitative storage phosphor autoradiography and are presented as histograms in FIG. 12.

Site-specific double-stranded cleavage of plasmid DNA. The plasmid pULHIV was prepared in order to determine whether 2'-deoxynebularine can be used to recognize CG base pairs within a larger fragment of double-helical DNA. For this, the purine-rich target sequence 5'd(AGAG$_2$CGAG$_4$CG$_2$)3' . 5'd(C$_2$GC$_4$TCGC$_2$TCT)3', a sequence which occurs naturally in the HIV genome (Ratner, L., et al. (1985) Nature 313:277–284), was cloned into pUC19 DNA. The ability of oligodeoxynucleotides 6–17 (FIG. 13) to bind specifically to the target sequence was examined by affinity cleaving. Conditions sensitive to the stability of the base triplet at the CG sites (2 μM oligodeoxynucleotide-EDTA, 1 mM spermine, 10 mM NaCl) were used. A 2.51 kbp EcoO109I-SspI restriction fragment of pULHIV, which contains the target sequence, located 0.42 kbp from the $^{32}$P radiolabeled end (FIG. 13), was isolated. This restriction fragment was allowed to react with 5'd(G$_2$Z2G$_4$Z1GZ2G$_2$Z1GT*)3' oligodeoxynucleotides-EDTA.Fe(II) 6–17, which differ at four variable positions (Z1=A, T or N; Z2=N, A, G, C, or T), in the presence of dithiothreitol at 37° C. (pH 7.4). The cleavage products were separated by 5% nondenaturing polyacrylamide gel electrophoresis. One major cleavage product, 0.42 kbp in size, indicated sequence specific cleavage was only observed for the oligodeoxynucleotides 6 (Z1=A; Z2=N), 10 (Z1=A; Z2=T), 11 (Z1=T; Z2=N), and 15 (Z1=T; Z2=T), respectively (results not shown).

It is to be understood that various other modifications will be apparent to and can readily be made by those skilled in the art, given the disclosure herein, without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A triple helix comprising a double-helical nucleic acid having more than 500 nucleotide base pairs and comprising first and second strands and a heteropolymeric oligonucleotide bound to a target sequence within said double-helical nucleic acid, wherein when said oligonucleotide is bound in a parallel orientation to said first strand, said oligonucleotide comprises a T or a C$^+$ bound to an A or a G respectively, on said first strand.

2. The triple helix of claim 1 wherein said oligonucleotide comprises a pyrimidine-rich oligonucleotide and said target sequence comprises a purine-rich sequence on one of the strands of said double-helical nucleic acid.

3. The triple helix of claim 2 wherein said pyrimidine-rich oligonucleotide binds to said target sequence in a parallel orientation to said purine-rich target sequence.

4. The triple helix of claim 1 wherein said oligonucleotide is bound in said parallel orientation to said first strand.

5. The triple helix of claim 1 wherein said oligonucleotide comprises a purine-rich oligonucleotide and said target sequence comprises a purine-rich sequence on one of the strands of said double-helical nucleic acid.

6. The triple helix of claim 5 wherein said purine-rich oligonucleotide binds to said target sequence in an antiparallel orientation to said purine-rich target sequence.

7. The triple helix of claim 6 wherein said purine-rich oligonucleotide contains a G when the nucleotide at the complementary position in said purine-rich target sequence is G and an A when the nucleotide at the complementary position in said purine-rich target sequence is A.

8. The triple helix of claim 7 wherein said purine-rich target sequence contains up to about 40% of the pyrimidine nucleotide C and said purine-rich oligonucleotide contains the pyrimidine nucleotide T when the nucleotide at the nucleotide at the complementary position in said purine-rich target sequence is C.

9. The triple helix of claim 8 wherein said purine-rich target sequence contains up to about 25% C.

10. The triple helix of claim 6 wherein said purine-rich target sequence contains one or more or the pyrimidine nucleotide C and said purine-rich oligonucleotide contains a G when the nucleotide at the complementary position in said purine-rich target sequence is G, an A or a T when the nucleotide at the complementary position in said purine-rich target sequence is an A and a nebularine nucleotide when the nucleotide at the complementary position in said purine-rich target sequence is C.

11. The triple helix of claim 1 wherein said oligonucleotide bound to said target sequence within said double-helical nucleic acid further comprises at least one nucleotide to which a moiety is attached.

12. The triple helix of claim 11 wherein said moiety is a detectable moiety.

13. The triple helix of claim 11 wherein said moiety is a cleaving moiety capable of causing cleavage of said double-helical nucleic acid.

14. The triple helix of claim 1 wherein said double-helical nucleic acid is an isolated nucleic acid.

15. The triple helix of claim 1 wherein said double-helical nucleic acid is substantially pure.

16. The triple helix of claim 1 wherein said target sequence comprises at least one purine nucleotide and at least one pyrimidine nucleotide.

17. The triple helix of claim 1 wherein said oligonucleotide is at least eleven nucleotides in length.

18. The triple helix of claim 1 wherein said oligonucleotide is at least fifteen nucleotides in length.

19. The triple helix of claim 1 wherein said oligonucleotide at least eighteen nucleotides in length.

20. A process for forming a triple helix wherein a heteropolymeric oligonucleotide is bound to a target sequence within a double-helical nucleic acid having more than 500 nucleotide base pairs and comprising first and second strands, comprising contacting said double-helical nucleic acid with a heteropolymeric oligonucleotide capable of binding to a target sequence contained within said double-helical nucleic acid, wherein when said oligonucleotide is bound in a parallel orientation to said first strand, said oligonucleotide comprises a T or a C$^+$ bound to an A or a G respectively, on said first strand.

21. The method claim 20 wherein said oligonucleotide comprises a pyrimidine-rich oligonucleotide and said target sequence comprises a purine-rich sequence on one of the strands of said double-helical nucleic acid.

22. The method of claim 21 wherein said pyrimidine-rich oligonucleotide binds to said target sequence in a parallel orientation to said purine-rich target sequence.

23. The method of claim 20 wherein said oligonucleotide is bound in said parallel orientation to said first strand.

24. The method of claim 20 wherein said oligonucleotide comprises a purine-rich oligonucleotide and said target sequence comprises a purine-rich sequence on one of the strands of said double-helical nucleic acid.

25. The method of claim 24 wherein said purine-rich oligonucleotide binds to said target sequence in an antiparallel orientation to said purine-rich target sequence.

26. The method of claim 25 wherein said purine-rich oligonucleotide contains a G when the nucleotide at the complementary position in said purine-rich target sequence is G and an A when the nucleotide at the complementary position in said purine-rich target sequence is an A.

27. The method of claim 26 wherein said purine-rich target sequence contains up to about 40% of the pyrimidine nucleotide C and said purine-rich oligonucleotide contains the pyrimidine nucleotide T when the nucleotide at the nucleotide at the complementary position in said purine-rich target sequence is C.

28. The method of claim 27 wherein said purine-rich target sequence contains up to about 25% C.

29. The method of claim 25 wherein said purine-rich target sequence contains one or more or the pyrimidine nucleotide C and said purine-rich oligonucleotide contains a G when the nucleotide at the complementary position in said purine-rich target sequence is G, an A or a T when the nucleotide at the complementary position in said purine-rich target sequence is an A and a nebularine nucleotide when the nucleotide at the complementary position in said purine-rich target sequence is C.

30. The method of claim 20 wherein said oligonucleotide bound to said target sequence within said double-helical nucleic acid further comprises at least one nucleotide to which a moiety is attached.

31. The method of claim 30 wherein said moiety is a detectable moiety.

32. The method of claim 30 wherein said moiety is a cleaving moiety capable of causing cleavage of said double-helical nucleic acid.

33. The process of claim 20 wherein said double-helical nucleic acid is an isolated nucleic acid.

34. The process of claim 20 wherein said double-helical nucleic acid is substantially pure.

35. A process for forming a triple-helix comprising contacting a triple-helical nucleic acid having more than 500 nucleotide base pairs with an oligonucleotide comprising a nebularine-containing nucleotide which is capable of binding to a target sequence contained within said double-helical nucleic acid.

* * * * *

UNITED STATES PATENT AND TRADEMARK OFFICE
CERTIFICATE OF CORRECTION

PATENT NO. : 5,874,555
DATED : February 23, 1999
INVENTOR(S) : DERVAN et al.

It is certified that error appears in the above-indentified patent and that said Letters Patent is hereby corrected as shown below:

Col. 5, line 32, delete "In FIG. 8B" and insert therefore --As can be seen, in FIG. 8B--.

Col. 16, line 64, delete "$\geq$" and insert therefore --$>$--.

Signed and Sealed this

Twenty-first Day of March, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO : 5,874,555
DATED : February 23, 1999
INVENTOR(S) : DERVAN et al.

It is certified that error appears in the above-identified patent and that said Letters Patent is hereby corrected as shown below:

Column 1, immediately preceding BACKGROUND OF THE INVENTION, insert a new paragraph to read –The U.S. Government has certain rights in this invention pursuant to Grant No. N00014-88-K-0441 awarded by the Department of the Navy and Grant No. GM 35724-13.–.

Signed and Sealed this

Fourth Day of July, 2000

Attest:

Attesting Officer

Q. TODD DICKINSON

Director of Patents and Trademarks